US010899825B2

(12) United States Patent
Marasco

(10) Patent No.: US 10,899,825 B2
(45) Date of Patent: *Jan. 26, 2021

(54) FLAVIVIRUS NEUTRALIZING ANTIBODIES AND METHODS OF USE THEREOF

(71) Applicant: Dana-Farber Cancer Institute, Inc., Boston, MA (US)

(72) Inventor: Wayne A. Marasco, Wellesley, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,439

(22) Filed: Jul. 17, 2019

(65) Prior Publication Data

US 2020/0062830 A1 Feb. 27, 2020

Related U.S. Application Data

(62) Division of application No. 15/818,491, filed on Nov. 20, 2017, now Pat. No. 10,400,032, which is a division of application No. 14/777,324, filed as application No. PCT/US2014/028310 on Mar. 14, 2014, now Pat. No. 9,822,166.

(60) Provisional application No. 61/792,336, filed on Mar. 15, 2013.

(51) Int. Cl.

| | |
|---|---|
| ***A61K 39/12*** | (2006.01) |
| ***C07K 16/10*** | (2006.01) |
| *A61K 39/00* | (2006.01) |

(52) U.S. Cl.

CPC .......... *C07K 16/1081* (2013.01); *A61K 39/12* (2013.01); *A61K 2039/505* (2013.01); *A61K 2039/545* (2013.01); *C07K 2317/24* (2013.01); *C07K 2317/524* (2013.01); *C07K 2317/565* (2013.01); *C07K 2317/71* (2013.01); *C07K 2317/76* (2013.01); *C12N 2770/24011* (2013.01); *Y02A 50/30* (2018.01)

(58) Field of Classification Search

None

See application file for complete search history.

(56) References Cited

U.S. PATENT DOCUMENTS

| | | | | |
|---|---|---|---|---|
| 9,822,166 | B2 * | 11/2017 | Marasco | C07K 16/1081 |
| 10,400,032 | B2 * | 9/2019 | Marasco | A61K 39/12 |

FOREIGN PATENT DOCUMENTS

| | | |
|---|---|---|
| WO | WO/05/032460 | * 4/2005 |
| WO | WO/05/123774 | * 12/2005 |

* cited by examiner

*Primary Examiner* — Benjamin P Blumel

(74) *Attorney, Agent, or Firm* — Baker Donelson

(57) ABSTRACT

The present invention provides antibodies that neutralize flavivirus and methods of use thereof. These antibodies are derived from mAbl 1 which recognizes West Nile virus E protein and is cross-reactive with members of the flavivirus family, including Denge virus. The antibodies of the present invention prevent antibody-dependent enhancement of a viral infection by having a modified Fc region that does not bind to the Fcγ receptor. The invented antibody is used to treat flaviviral infections and symptoms thereof.

34 Claims, 6 Drawing Sheets

Specification includes a Sequence Listing.

FLAVIVIRUS NEUTRALIZING ANTIBODIES AND METHODS OF USE THEREOF

RELATED APPLICATIONS

This application is a divisional application of U.S. patent application Ser. No. 15/818,491, filed on Nov. 20, 2017, now issued as U.S. Pat. No. 10,400,032, which is a divisional application of U.S. patent application Ser. No. 14/777,324, filed on Sep. 15, 2015, now issued as U.S. Pat. No. 9,822,166, which is a national stage application filed under 35 U.S.C. § 371 of International Application No. PCT/US2014/028310, filed on Mar. 14, 2014, which claims benefit of, and priority to, U.S. provisional patent application No. 61/792,336 filed on Mar. 15, 2013; the contents of each which are hereby incorporated by reference in their entireties.

GOVERNMENT INTEREST

This invention was made with government support under grant number AI070343 awarded by The National Institutes of Health. The government has certain rights in the invention.

INCORPORATION OF SEQUENCE LISTING

The contents of the file named "DFCI-073_N01US 322270-2532_ST25.txt", which was created on Sep. 15, 2015 and is 28 KB in size, are hereby incorporated by reference in their entireties.

FIELD OF THE INVENTION

This invention relates generally to flavivirus neutralizing antibodies as well as to methods for use thereof.

BACKGROUND OF THE INVENTION

Flaviviruses, such as West Nile virus and Dengue virus, present a significant threat to global health. West Nile virus causes a febrile illness that can lead to fatal meningitis or encephalitis across multiple species. West Nile virus can be carried by both birds and mosquitos, which has allowed its spread at an alarming pace worldwide. Similarly, four serotypes of Dengue virus can be transmitted through mosquito bites, and causes tens of millions of human cases of dengue annually, including 500,000 hospitalizations and 20,000 deaths, with an economic burden rivalling that of malaria.

Vaccines and antibody therapeutics are currently in development to prevent and treat flavivirus infection. However, evidence from dengue virus infections indicate that vaccination strategies for flaviviruses may not be as straightforward as other viruses. A first infection with one Dengue virus serotype induces protective immunity to the homologous serotype. However, there is no cross-protection against infection by a different serotype. Instead, pre-existing immunity is associated with increased risk of infection and illness due to antibody-dependent enhancement (ADE) of infection. In ADE, antibodies raised by prior flavivirus infection or passively transferred from mother to child cause an increased rate of infection and pathogenicity. Thus, conventional methods of antibody-based therapeutics or vaccines against flavivirus may exponentially increase incidence of flavivirus infection and illness.

Accordingly, there is an urgent need for therapeutics and methods for preventing flavivirus infection, and diseases and disorders related thereto, without increasing the risk of antibody-dependent enhancement of infection.

SUMMARY OF THE INVENTION

The invention is based upon the discovery of monoclonal antibodies which bind and neutralize flavivirus, and do not contribute to the antibody-dependent enhancement of flavivirus infection. The monoclonal antibody is fully human. The antibodies recognize the West Nile virus envelope protein E (WNE), and have broad cross-reactivity across other members of the flavivirus family. Importantly, the antibodies contain mutations in the Fc region that prevent binding to the Fcγ receptor. The antibodies are referred to herein as huFV antibodies.

The invention provides an isolated humanized monoclonal antibody having a heavy chain with three CDRs, wherein the CDR1 includes amino acid sequence GYSTH (SEQ ID NO:21), wherein the CDR2 includes amino acid sequence WDNPSSGDTTYAENFRG (SEQ ID NO:22), and wherein the CDR3 includes amino acid sequence GGDDYSFDH (SEQ ID NO:23) respectively; a light chain with three CDRs, wherein the CDR1 includes amino acid sequence RGDSLRSYYAS (SEQ ID NO:24), wherein the CDR2 includes amino acid sequence GENNRPS (SEQ ID NO:25), and wherein the CDR3 includes amino acid sequence NSRDSSDHLLL (SEQ ID NO:26) respectively. The antibody has a modified Fc region such that the Fc region does not bind to the Fcγ receptor, and binds to a flavivirus. Exemplary Fc regions are disclosed herein.

In one aspect, the invention provides an isolated humanized monoclonal antibody having a $V_H$ amino acid sequence having SEQ ID NO: 1, a $V_L$ amino acid sequence having SEQ ID NO: 3. In another aspect, the invention provides an isolated humanized monoclonal antibody comprising a $V_H$ nucleotide sequence having SEQ ID NO: 2, a $V_L$ nucleotide sequence having SEQ ID NO: 4. The antibody further comprises a modified Fc region such that the Fc region does not bind to the Fcγ receptor, and binds to a flavivirus.

The present invention provides an isolated humanized monoclonal antibody that neutralizes a flavivirus.

The present invention provides antibodies with a modified Fc region such that the Fc region does not bind to the Fcγ receptor. The modified Fc region contains mutations at amino acid positions 234 and 235. In one aspect, the mutations are L234A and L235A. In one embodiment, the modified Fc region comprises a CH2 region wherein the amino acids at positions 4 and 5 of the CH2 region are mutated. For example, the leucine amino acids at positions 4 and 5 are mutated to a different amino acid, preferably, an alanine. In other embodiments, the modified Fc region comprises an Fc region where the amino acids at positions 108 and 109 are mutated. For example, the leucines at positions 108 and 109 of the Fc region are mutated to a different amino acid, preferably, an alanine. In another embodiment, the modified Fc region comprises the amino acid sequence of SEQ ID NO: 7. The modified Fc region binds to the neonatal Fc receptor (FcRn).

In one aspect, the antibody does not contribute to an antibody-dependent enhancement of a flavivirus infection.

In one aspect, the antibody is linked to a therapeutic agent. The therapeutic agent is a toxin, a radiolabel, a siRNA, a small molecule, or a cytokine. For example, the cytokine is TGF-beta.

The present invention further provides a cell producing a huFV antibody. The cell may be a mammalian cell (i.e., a mouse, rabbit, goat, or sheep), or a plant cell (i.e. tobacco plant).

The present invention provides a method for preventing antibody-dependent enhancement of a flavivirus infection by administering a huFv antibody to a subject. In one aspect, the antibody is administered after a first infection by a flavivirus.

Additionally, the present invention provides a method of increasing vaccine efficiency by administering to a subject a huFV antibody and a vaccine. In one aspect, the huFV antibody and the vaccine are administered sequentially or concurrently. In one aspect, the vaccine is a viral vaccine.

The present invention further provides a method for treating or alleviating a symptom of a flavivirus infection by administering to a subject in need thereof a composition containing a huFV antibody. In another aspect, the present invention features a method for delaying the onset or progression of one or more symptoms of a flavivirus infection. Symptoms of flavivirus infection include, but are not limited to, weight loss, paralysis, fever, headaches, nausea, vomiting, skin rash, and body aches. In one aspect, an anti-viral agent is also administered to the subject. In one aspect, the huFV antibody and the anti-viral agent are administered sequentially or concurrently. The anti-viral agent is an antibody, an antibody linked to a therapeutic agent, or a small molecule.

The flavivirus is West Nile virus, Dengue virus (serotypes 1-4), St. Louis encephalitis virus, yellow fever virus, Japanese encephalitis virus, and Murray Valley encephalitis virus.

The invention further provides a nucleic acid sequence containing a nucleic acid sequence of SEQ ID NO: 2, 4 and 8.

The invention further provides a nucleic acid sequence encoding a polypeptide of SEQ ID NO: 1 and 3. The invention further provides a polypeptide containing the amino acid sequence of SEQ ID NO: 1, 3 and 7.

The invention further provides a vector containing the nucleic acid sequence containing SEQ ID NO: 2, 4 and 8, or encoding a polypeptide of SEQ ID NO: 1, 3 and 7.

Additionally, the invention provides a cell containing a vector containing the nucleic acid sequence containing SEQ ID NO: 2, 4 and 8, or encoding a polypeptide of SEQ ID NO: 1, 3 and 7.

Other features and advantages of the invention will be apparent from and are encompassed by the following detailed description and claims.

DETAILED DESCRIPTION

Figure 1:
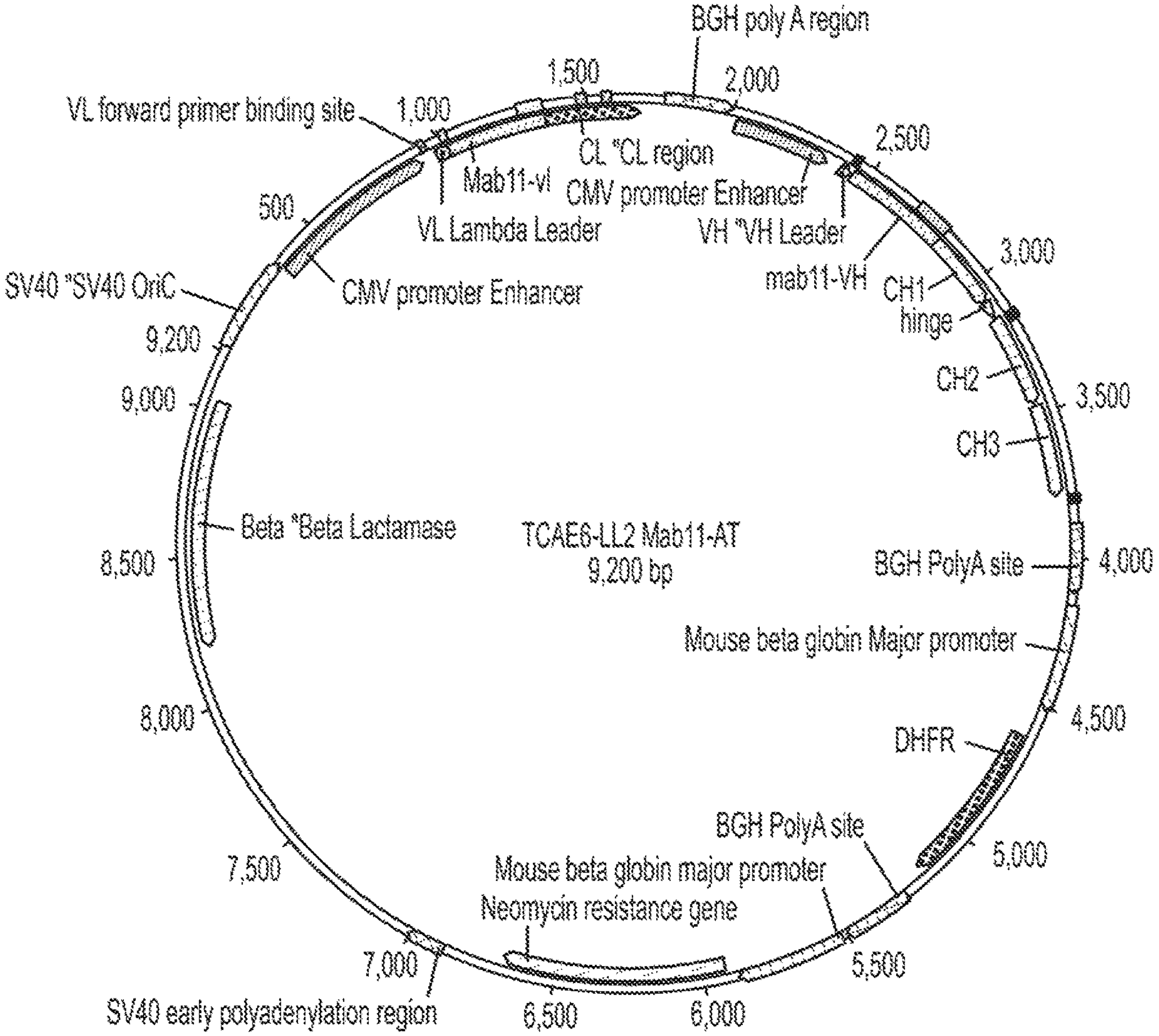
FIG. 1 shows a schematic of an expression vector containing wild-type mAb-11.
Figure 2:
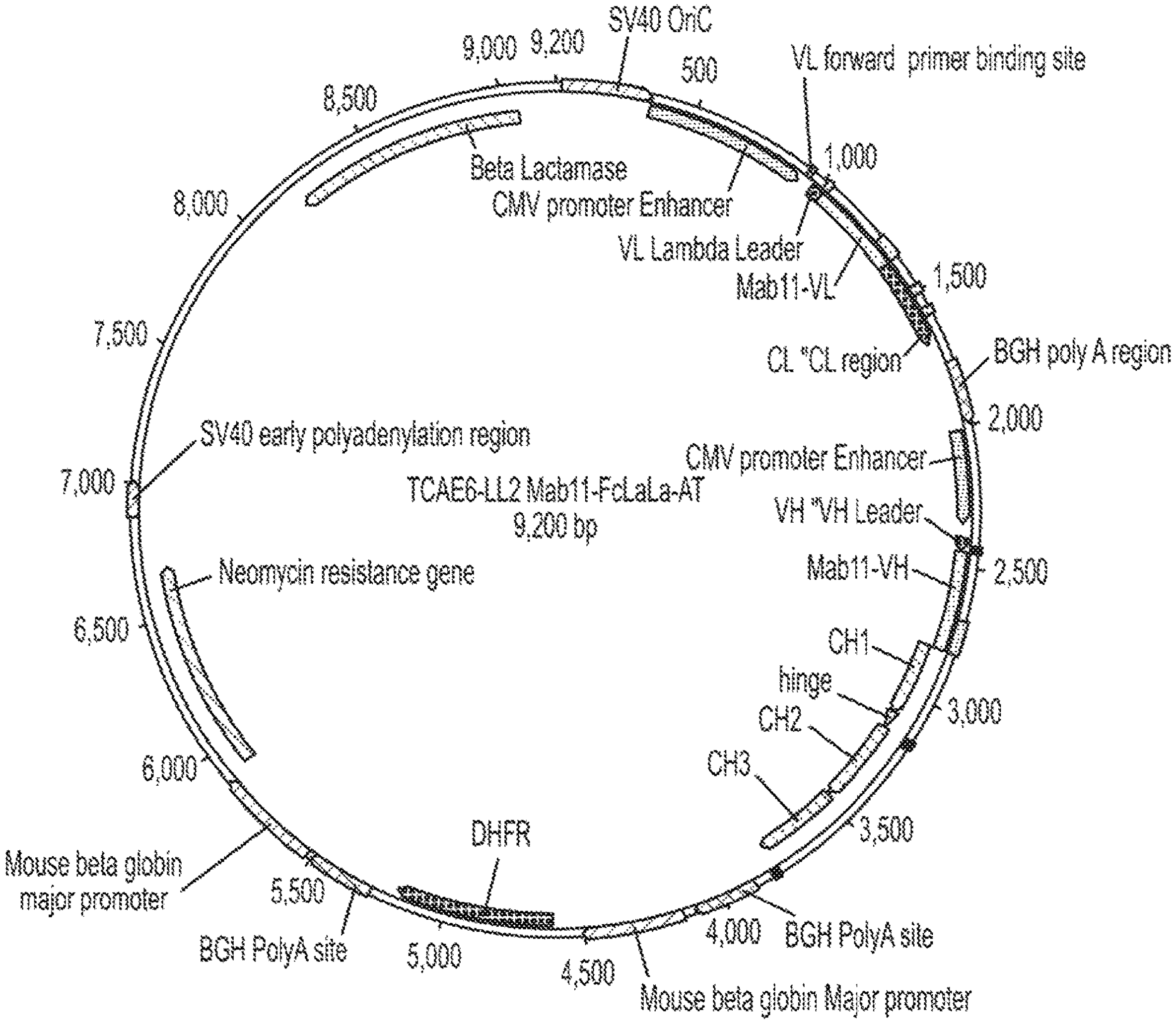
FIG. 2 shows a schematic of an expression vector containing engineered mAb-11-LALA.

The present invention provides antibodies that neutralize infection by members of the flavivirus family without contributing to antibody-dependent enhancement of virus infection. Antibodies that bind and neutralize West Nile virus are described in International Publication WO 2005/123774, the contents of which are incorporated by reference in its entirety. The antibodies of the present invention were produced by modifying an antibody against West Nile virus, mAb11, such that the Fc region of the antibody does not bind to the Fc-gamma receptor. Thus, the modified antibody does not contribute to antibody-dependent enhancement of infection. The antibodies and methods disclosed herein relate to this antibody, and methods for treating or preventing an infection by a flavivirus, and related diseases and disorders. The antibody of the present invention, mAB11-LALA has demonstrated increased capability of preventing and treating flavivirus infection compared to the wild-type mAb11, as described herein and demonstrated in the examples.

MAb11 was identified using a phage display screening and binds to the West Nile virus envelope protein E, within the DI and DII domains and specifically at the fusion loop peptide (Gould et al., Journal of Virology, 2005, 79(23): 14606-14613; Sultana et al., Journal of Immunology, 2009, 183: 650-660, the contents of which are incorporated herein in their entirety). The engineered mAb11 antibody with mutations at amino acids positions 234 and 235 in the Fc region is referred to herein as “mAb11-LALA”.

The antibodies of the present invention have broad cross-reactivity to the members of the Flavivirus family. For example, the antibody demonstrates cross-reactivity and neutralization of several different flaviviruses, including, but not limited to West Nile virus, Dengue virus (serotypes 1, 2, 3 and 4), St. Louis encephalitis virus, yellow fever virus, Japanese encephalitis virus, and Murray Valley encephalitis virus.

Neutralizing antibodies have been and are being currently developed for the treatment and prevention of viral infections, specifically infections by members of the Flavivirus genus. Initial studies have demonstrated that such antibodies show increased neutralization and protection from infection by flavivirus family members (i.e., West Nile Virus or one of the four Dengue virus serotypes). However, subsequent virus challenge studies, in which experimental subjects were treated with neutralizing antibodies and then challenged with doses of flavivirus (i.e., Dengue virus), did not show a decrease in viremia. In some cases, treatment with such antibodies resulted in enhancement of infection compared to controls, which is believed to be mediated though a mechanism called antibody-dependent enhancement (ADE). These results demonstrate the importance of developing therapeutics and methods that prevent antibody-dependent enhancement of flavivirus infection.

Antibody-dependent enhancement of infection can be accomplished by the binding of the Fc region of the antibody to an Fcγ receptor (FcγR) on a host cell. Infectious viral particles bound to these antibodies are therefore more efficiently brought to host cells by Fc region-Fc receptor binding. This increases the infection and replication rate of the virus, thereby enhancing the infectivity and pathogenicity of the virus.

In contrast to standard anti-viral antibodies, the antibodies of the present invention have reduced binding to the Fcγ receptors (FcγR) or do not bind to the FcγR. Fcγ receptors include, for example, FcγRI, FcγRIIIa, FcγRIIIb, and FcγRIIIc. In one embodiment, the antibodies of the invention contain one or more mutations in the Fc region. The mutation(s) may be any mutation that reduces or abrogates binding of the antibody to a FcγR. Mutations can be substitutions, additions, or deletions of amino acids in the Fc region. Although the antibodies of the present invention have mutated Fc regions, the antibodies still confer potent flavivirus neutralization.

The Fc region of an antibody comprises two domains, CH2 and CH3. These domains, or specific amino acids within these domains known in the art, mediate the interaction with FcγR. Antibodies of the present invention contain any mutation (i.e., substitution, addition, or deletion of one or more than one amino acid) in the CH2 or CH3 domain, or both, that reduces or abrogates the binding of the antibody to an FcγR. For example, antibodies of the present invention contain a mutation or substitution of at least one amino acid at positions 233, 234, 235, 236, 237, 250, 314, or 428 of the wild-type Fc region. Preferably, the amino acid substitution is to an alanine.

In one embodiment, the Fc region of an antibody of the invention comprises a substitution at positions 234 or 235 of the heavy chain of the antibody, or both. In general, the amino acid at positions 234 and 235 of the wild-type Fc region is a leucine ("L"). In one embodiment, the antibodies of the invention comprise an amino acid at position 234, 235, or both, that is not a leucine. In another embodiment, the antibodies of the invention comprise an alanine ("A") at position 234, 235 or both. An antibody comprising the mutations at positions 234 and 235 of the Fc region where the leucines are mutated to alanines is referred to herein as a "LALA" variant.

In a preferred embodiment, the antibodies of the present invention are full length, or intact, antibodies, wherein the antibodies contain an antigen-binding region (i.e., Fab region or Fab fragment) and an Fc region (modified or mutated, as described herein). Previously developed antibodies in the art that were designed to circumvent ADE often lack the Fc region to prevent binding to FcγR. Antibodies of the present invention provide superior properties by retaining the Fc region. One such property is the ability to bind to the neonatal receptor (FcRn) expressed on endothelial cells, which plays a critical role in the homeostasis of circulating IgG levels. Binding of circulating antibodies to the FcRn induces internalization through pinocytosis, in which the antibodies are recycled to the cell surface, and released at the basic pH of blood. This mechanism protects the antibodies of the present invention from degradation and increases the half-life compared to other unmodified antibodies or antibody fragments lacking the Fc region. Increased persistence of the antibodies of the present invention in the serum provides increased efficacy by allowing higher circulating levels, less frequent administration, and reduced doses. Another property of the antibodies of the present invention may include the ability to bind to complement factors. Binding of complement factors, such as C1q, to the Fc region of the antibody triggers a signaling cascade to activate complement-dependent cytotoxicity (CDC).

It is known in the art that the binding sites on the Fc region of Fcγ receptors is distinct from the binding site of the neonatal Fc receptor (FcRn). Therefore, the antibodies of the present invention have Fc regions modified such that they have reduced binding or cannot bind to the Fcγ receptors, however are still competent for binding to the FcRn receptor. Antibodies of the invention can be modified by introducing random amino acid mutations into particular region of the CH2 or CH3 domain of the heavy chain in order to alter their binding affinity for FcγR and/or FcRn and/or their serum half-life in comparison to the unmodified antibodies. Examples of such modifications include, but are not limited to, substitutions of at least one amino acid from the heavy chain region selected from the group consisting of amino acid residues 234, 235, 236, 237, 250, 314, and 428. Accordingly, the antibodies of the present invention have greater half-life than unmodified antibodies, which confers increased efficacy in the prevention and treatment of flavivirus infections and subsequent disease.

In one aspect, the antibodies of the present invention have Fc regions modified such that have reduced binding or cannot bind to the Fcγ receptors, however are still competent for binding to complement factors, such as C1q.

One of ordinarily skill in the art could readily prepare the modified antibodies of the present invention. Recombinant DNA techniques for introducing mutations or substitutions in the Fc region of an antibody are known in the art. Characterization of the Fc region for their ability to bind or not bind to Fc receptors (Fcγr or FcRn) can be readily performed by the ordinarily skilled artisan, for example by immunoprecipitation, immunoassay, affinity chromatography, or array techniques.

The humanized antibodies described herein may be produced in mammalian expression systems, such as hybridomas. The humanized antibodies described herein may also be produced by non-mammalian expression systems, for example, by transgenic plants. For example, the antibodies described herein are produced in transformed tobacco plants (*N. benthamiana* and *N. tabaccum*).

The various nucleic acid and amino acid sequences of mAb11 of the present invention is provided below:

Heavy Chain Variable ($V_H$) Amino Acid Sequence: (SEQ ID NO: 1)

```
TRVLSQVQLVQSGAEVKKPGASVKVSCKASGYTFSGYSTHWLRQVPGQ
GLEWIGWDNPSSGDTTYAENFRGRVTLTRDTSITTDYLEVRGLRSDDT
AVYYCARGGDDYSFDHWGQGTLVTVSS
```

-continued

Heavy Chain Variable ($V_H$) Nucleic Acid Sequence:

(SEQ ID NO: 2)

caggtgcagctggtgcagtctggggctgaggtgaagaagcctggggcc tcagtgaaagtctectgcaaggcttctggatacaccttcageggctac tctacacactggctgcgacaggtecctggacagggacttgagtggatt ggatgggacaaccctagtagtggtgacacgacctatgeagagaatffi cggggcagggtcaccetgaccagggacacgtccatcaccacagattac ttggaagtgaggggtetaagatctgacgacacggccgtetattattgl gccagaggeggagatgactacagctttgaccattggggtcagggcacc ctggtcaccgtctcctca Light Chain Variable ($V_H$) Amino Acid Sequence:

(SEQ ID NO: 3)

SSELTQDPAVSVALGQTVRITCRGDSLRSYYASWYQQKPGQAPVLVIY

GENNRPSGIPDRFSGSSSGDTASLTITGAQAEDEADYYCNSRDSSDHL

LLFGQGTKL

Light Chain Variable ($V_H$) Nucleic Acid Sequence:

(SEQ ID NO: 4)

Tcttctgagctgactcaggacccagctgtgtctgtggccttgggacag acagtcaggatcacatgccgaggagacagcctcagaagttattatgca agctggtaccaacagaagccaggacaggcccctgtacttgtcatctat ggtgaaaacaaccgaccctcagggatcccagaccgattctctggctcc agctcaggagacacagcttccttgaccatcactggggctcaggcggaa gatgaggctgactattactgtaactcccgggacagcagtgatcacctt ctcctattcggtggagggaccaagttgaccgtcctaggt The Fc region comprises three heavy constant domains, CH1, CH2 or CH3 domains. A hinge region joins the CH1 and CH2 regions. Exemplary Fc region sequences for wild-type and modified Fc regions with respect to the invention are provided below.

The amino acid sequence of the Fc Region of wild-type mAb-11 is provided as follows:

(SEQ ID NO: 5)

ASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDK

KAEPKSCDKTHTCPPCPAPELLGGPSVFLFPPKPKDTLMISRTPEVTC

VVVDVSHEDPEVKFNWYVDGVEVHNAKTKPREEQYNSTYRVVSVLTVL

HQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFF

LYSKLTVDKSRWQQGNVFSCSVMHEALHNHYTQKSLSLSPGK

The nucleic acid sequence of the Fc Region of wild-type mAb-11 is provided as follows:

(SEQ ID NO: 6)

CTAGCACCAAGGGCCCATCGGTCTTCCCCCTGGCACCCTCCTCCAAGAGC

ACCTCTGGGGGCACAGCGGCCCTGGGCTGCCTGGTCAAGGACTACTTCCC

CGAACCGGTGACGGTGTCGTGGAACTCAGGCGCCCTGACCAGCGGCGTGC

-continued

ACACCTTCCCGGCTGTCCTACAGTCCTCAGGACTCTACTCCCTCAGCAGC

GTGGTGACCGTGCCCTCCAGCAGCTTGGGCACCCAGACCTACATCTGCAA

CGTGAATCACAAGCCCAGCAACACCAAGGTGGACAAGAAAGCAGAGCCCA

AATCTTGTGACAAAACTCACACATGCCCACCGTGCCCAGCACCTGAACTC

CTGGGGGGACCGTCAGTCTTCCTCTTCCCCCCAAAACCCAAGGACACCCT

CATGATCTCCCGGACCCCTGAGGTCACATGCGTGGTGGTGGACGTGAGCC

ACGAAGACCCTGAGGTCAAGTTCAACTGGTACGTGGACGGCGTGGAGGTG

CATAATGCCAAGACAAAGCCGCGGGAGGAGCAGTACAACAGCACGTACCG

TGTGGTCAGCGTCCTCACCGTCCTGCACCAGGACTGGCTGAATGGCAAGG

AGTACAAGTGCAAGGTCTCCAACAAAGCCCTCCCAGCCCCCATCGAGAAA

ACCATCTCCAAAGCCAAAGGGCAGCCCCGAGAACCACAGGTGTACACCCT

GCCCCCATCCCGGGATGAGCTGACCAAGAACCAGGTCAGCCTGACCTGCC

TGGTCAAAGGCTTCTATCCCAGCGACATCGCCGTGGAGTGGGAGAGCAAT

GGGCAGCCGGAGAACAACTACAAGACCACGCCTCCCGTGCTGGACTCCGA

CGGCTCCTTCTTCCTCTACAGCAAGCTCACCGTGGACAAGAGCAGGTGGC

AGCAGGGGAACGTCTTCTCATGCTCCGTGATGCATGAGGCTCTGCACAAC

CACTACACGCAGAAGAGCCTCTCCCTGTCTCCGGGTAAATGA

The amino acid sequence of the modified Fc region of mAb-11-LALA is provided below. For example, the amino acids at positions 108 and 109 are mutated. In the sequence provided below, the leucine amino acids at position 108 and 109 are mutated to alanines (underlined).

(SEQ ID NO: 7)

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKAEP

KSCDKTHTCPPCPAPEAAGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

The nucleic acid sequence of the modified Fc region of mAb-11-LALA is provided below. For example, the amino acids at positions 108 and 109 encoded by the provided nucleic acid sequence are mutated from leucines to alanines (underlined).

(SEQ ID NO: 8)

CTAGCACCAAGGGCCCATCGGTCTTCCCCCTGGCACCCTCCTCCAAGAGC

ACCTCTGGGGGCACAGCGGCCCTGGGCTGCCTGGTCAAGGACTACTTCCC

CGAACCGGTGACGGTGTCGTGGAACTCAGGCGCCCTGACCAGCGGCGTGC

ACACCTTCCCGGCTGTCCTACAGTCCTCAGGACTCTACTCCCTCAGCAGC

GTGGTGACCGTGCCCTCCAGCAGCTTGGGCACCCAGACCTACATCTGCAA

CGTGAATCACAAGCCCAGCAACACCAAGGTGGACAAGAAAGCAGAGCCCA

AATCTTGTGACAAAACTCACACATGCCCACCGTGCCCAGCACCTGAAGCC

-continued

GCCGGGGGACCGTCAGTCTTCCTCTTCCCCCCAAAACCCAAGGACACCCT
CATGATCTCCCGGACCCCTGAGGTCACATGCGTGGTGGTGGACGTGAGCC
ACGAAGACCCTGAGGTCAAGTTCAACTGGTACGTGGACGGCGTGGAGGTG
CATAATGCCAAGACAAAGCCGCGGGAGGAGCAGTACAACAGCACGTACCG
TGTGGTCAGCGTCCTCACCGTCCTGCACCAGGACTGGCTGAATGGCAAGG
AGTACAAGTGCAAGGTCTCCAACAAAGCCCTCCCAGCCCCCATCGAGAAA
ACCATCTCCAAAGCCAAAGGGCAGCCCCGAGAACCACAGGTGTACACCCT
GCCCCCATCCCGGGATGAGCTGACCAAGAACCAGGTCAGCCTGACCTGCC
TGGTCAAAGGCTTCTATCCCAGCGACATCGCCGTGGAGTGGGAGAGCAAT
GGGCAGCCGGAGAACAACTACAAGACCACGCCTCCCGTGCTGGACTCCGA
CGGCTCCTTCTTCCTCTACAGCAAGCTCACCGTGGACAAGAGCAGGTGGC
AGCAGGGGAACGTCTTCTCATGCTCCGTGATGCATGAGGCTCTGCACAAC
CACTACACGCAGAAGAGCCTCTCCCTGTCTCCGGGTAAATGA

The amino acid sequence for the CH1 region is provided below:

(SEQ ID NO: 9)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKK

The nucleic acid sequence for the CH1 region is provided below:

(SEQ ID NO: 10)
CTAGCACCAAGGGCCCATCGGTCTTCCCCCTGGCACCCTCCTCCAAGAGC
ACCTCTGGGGGCACAGCGGCCCTGGGCTGCCTGGTCAAGGACTACTTCCC
CGAACCGGTGACGGTGTCGTGGAACTCAGGCGCCCTGACCAGCGGCGTGC
ACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAA
CGTGAATCACAAGCCCAGCAACACCAAGGTGGACAAGAAA

The mAb11 antibody described herein may comprise a mutation specifically in the CH2 region that reduces or inhibits binding to the Fcγ receptor. Preferably, the mutation does not affect binding to FcRn receptor. Preferably, the mAb11 antibody contains two mutations in the CH2 region, such that two adjacent lysines are mutated to alanines described below. For example, the mutations are located at amino acid positions 4 and 5 of the CH2 region. Preferably, the mutations are to alanines.

The amino acid sequence for the CH2 region of the wild-type mAb11 antibody is provided below:

(SEQ ID NO: 11)
APELLGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAK

The nucleic acid sequence for the CH2 region of the wild-type mAb11 antibody is provided below:

(SEQ ID NO: 12)
GCACCTGAACTCCTGGGGGGACCGTCAGTCTTCCTCTTCCCCCCAAAACC
CAAGGACACCCTCATGATCTCCCGGACCCCTGAGGTCACATGCGTGGTGG
TGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAA
CAGCACGTACCGTGTGGTCAGCGTCCTCACCGTCCTGCACCAGGACTGGC
TGAATGGCAAGGAGTACAAGTGCAAGGTCTCCAACAAAGCCCTCCCAGCC
CCCATCGAGAAAACCATCTCCAAAGCCAAA

The amino acid sequence for the CH2 region of the mutant mAb11 antibody is provided below (the LALA mutation is underlined):

(SEQ ID NO: 13)
APEAAGGPSVFLFPPKPKDTLMISRTPEVTCVVVDVSHEDPEVKFNWYVD
GVEVHNAKTKPREEQYNSTYRVVSVLTVLHQDWLNGKEYKCKVSNKALPA
PIEKTISKAK

The nucleic acid sequence for the CH2 region of the mutant mAb11 antibody is provided below (the LALA mutation is underlined):

(SEQ ID NO: 14)
GCACCTGAAGCCGCCGGGGGACCGTCAGTCTTCCTCTTCCCCCCAAAACC
CAAGGACACCCTCATGATCTCCCGGACCCCTGAGGTCACATGCGTGGTGG
TGGACGTGAGCCACGAAGACCCTGAGGTCAAGTTCAACTGGTACGTGGAC
GGCGTGGAGGTGCATAATGCCAAGACAAAGCCGCGGGAGGAGCAGTACAA
CAGCACGTACCGTGTGGTCAGCGTCCTCACCGTCCTGCACCAGGACTGGC
TGAATGGCAAGGAGTACAAGTGCAAGGTCTCCAACAAAGCCCTCCCAGCC
CCCATCGAGAAAACCATCTCCAAAGCCAAA

The amino acid sequence for the CH3 region of the mAb11 antibody is provided below:

(SEQ ID NO: 15)
GQPREPQVYTLPPSRDELTKNQVSLTCLVKGFYPSDIAVEWESNGQPENN
YKTTPPVLDSDGSFFLYSKLTVDKSRWQQGNVFSCSVMHEALHNHYTQKS
LSLSPGK

The nucleic acid sequence for the CH3 region of the mAb11 antibody is provided below:

(SEQ ID NO: 16)
GGGCAGCCCCGAGAACCACAGGTGTACACCCTGCCCCCATCCCGGGATGA
GCTGACCAAGAACCAGGTCAGCCTGACCTGCCTGGTCAAAGGCTTCTATC
CCAGCGACATCGCCGTGGAGTGGGAGAGCAATGGGCAGCCGGAGAACAAC
TACAAGACCACGCCTCCCGTGCTGGACTCCGACGGCTCCTTCTTCCTCTA
CAGCAAGCTCACCGTGGACAAGAGCAGGTGGCAGCAGGGGAACGTCTTCT
CATGCTCCGTGATGCATGAGGCTCTGCACAACCACTACACGCAGAAGAGC
CTCTCCCTGTCTCCGGGTAAATGA

The amino acid sequence for the hinge region is provided below:

```
(SEQ ID NO: 17)
AEPKSCDKTHTCPPCP
```

The nucleic acid sequence for the hinge region is provided below:

```
(SEQ ID NO: 18)
GCAGAGCCCAAATCTTGTGACAAAACTCACACATGCCCACCGTGCCCA
```

The amino acid sequence of the heavy chain (including both variable and constant regions) of wild-type mAb-11 is provided below:

```
(SEQ ID NO: 19)
TRVLSQVQLVQSGAEVKKPGASVKVSCKASGYTFSGYSTHWLRQVPGQGL

EWIGWDNPSSGDTTYAENFRGRVTLTRDTSITTDYLEVRGLRSDDTAVYY

CARGGDDYSFDHWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKAEPKSCDKTHTCPPCPAPELLGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLS

PGK
```

The amino acid sequence of the heavy chain (including both variable and constant regions) of mutant mAb-11 is provided below (LALA mutation is underlined):

```
(SEQ ID NO: 20)
TRVLSQVQLVQSGAEVKKPGASVKVSCKASGYTFSGYSTHWLRQVPGQGL

EWIGWDNPSSGDTTYAENFRGRVTLTRDTSITTDYLEVRGLRSDDTAVYY

CARGGDDYSFDHWGQGTLVTVSSASTKGPSVFPLAPSSKSTSGGTAALGC

LVKDYFPEPVTVSWNSGALTSGVHTFPAVLQSSGLYSLSSVVTVPSSSLG

TQTYICNVNHKPSNTKVDKKAEPKSCDKTHTCPPCPAPEAAGGPSVFLFP

PKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPR

EPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLS

PGK
```

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, and chimeric antibodies In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "epitope" includes any protein determinant capable of specific binding to an immunoglobulin, a scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a flavivirus epitope when the equilibrium binding constant ($K_d$) is ≤1 μM, preferably ≤100 nM, more preferably ≤10 nM, and most preferably ≤100 μM to about 1 μM, as measured by assays such as radioligand binding assays or similar assays known to those skilled in the art.

An flavivirus protein (i.e., an envelope protein or West Nile envelope protein E) of the invention, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention by ascertaining whether the former prevents the latter from binding to flavivirus. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the flavivirus envelope proteins, such as West Nile virus protein E, with which it is normally reactive, and then add the human monoclonal antibody being tested to determine if the human monoclonal antibody being tested is inhibited in its ability to bind flavivirus envelope proteins, such as West Nile virus E. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out by utilizing WNE and determining whether the test monoclonal antibody is able to neutralize members of the flavivirus family.

Various procedures known within the art may be used for the production of polyclonal or monoclonal antibodies directed against a protein of the invention, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "humanized antibodies", "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: Monoclonal Antibodies and Cancer Therapy, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: Monoclonal Antibodies and Cancer Therapy, Alan R. Liss, Inc., pp. 77-96).

In addition, humanized antibodies can be produced in transgenic plants, as an an inexpensive production alternative to existing mammalian systems. For example, the transgenic plant may be a tobacco plant, i.e., *Nicotiania benthamiana*, and *Nicotiana tabaccum*. The antibodies are purified from the plant leaves. Stable transformation of the plants can be achieved through the use of *Agrobacterium tumefaciens* or particle bombardment. For example, nucleic acid expression vectors containing at least the heavy and light chain sequences are expressed in bacterial cultures, i.e., *A. tumefaciens* strain BLA4404, via transformation. Infiltration of the plants can be accomplished via injection. Soluble leaf extracts can be prepared by grinding leaf tissue in a mortar and by centrifugation. Isolation and purification of the antibodies can be readily be performed by many of the methods known to the skilled artisan in the art. Other methods for antibody production in plants are described in, for example, Fischer et al., Vaccine, 2003, 21:820-5; and Ko et al, Current Topics in Microbiology and Immunology, Vol. 332, 2009, pp. 55-78. As such, the present invention further provides any cell or plant comprising a vector that encodes the antibody of the present invention, or produces the antibody of the present invention.

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of flavivirus in a sample. The antibody can also be used to try to bind to and disrupt flavivirus envelope protein activity.

In a preferred embodiment, the antibodies of the present invention are full-length antibodies, containing an Fc region similar to wild-type Fc regions that bind to Fc receptors.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in neutralizing or preventing viral infection. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)). In a preferred embodiment, the antibody of the present invention has modifications of the Fc region, such that the Fc region does not bind to the Fc receptors. Preferably, the Fc receptor is Fcγ receptor. Particularly preferred are antibodies with modification of the Fc region such that the Fc region does not bind to Fcγ, but still binds to neonatal Fc receptor.

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{13}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against Flaviviruses

Methods for the screening of antibodies that possess the desired specificity include, but are not limited to, enzyme linked immunosorbent assay (ELISA) and other immunologically mediated techniques known within the art.

Antibodies directed against a flavivirus envelope protein such as WNE (or a fragment thereof) may be used in methods known within the art relating to the localization and/or quantitation of a flavivirus envelope protein such as WNE (e.g., for use in measuring levels of the flavivirus protein within appropriate physiological samples, for use in diagnostic methods, for use in imaging the protein, and the like). In a given embodiment, antibodies specific to an flavivirus envelope protein such as WNE, or derivative, fragment, analog or homolog thereof, that contain the antibody derived antigen binding domain, are utilized as pharmacologically active compounds (referred to hereinafter as "Therapeutics").

An antibody specific for a flavivirus envelope protein such as WNE of the invention can be used to isolate a flavivirus polypeptide by standard techniques, such as immunoaffinity, chromatography or immunoprecipitation. Antibodies directed against an flavivirus protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, (3-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention, including polyclonal, monoclonal, humanized and fully human antibodies, may used as therapeutic agents. Such agents will generally be employed to treat or prevent a flavivirus-related disease or pathology (e.g., dengue fever) in a subject. An antibody preparation, preferably one having high specificity and high affinity for its target antigen, is administered to the subject and will generally have an effect due to its binding with the target. Administration of the antibody may abrogate or inhibit or interfere with the internalization of the virus into a cell. In this case, the antibody binds to the target and prevents binding to an Fc receptor-expressing cell, thereby blocking fusion the virus to the cell membrane inhibiting internalization of the virus in antibody-dependent enhancement of infection.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding a flavivirus protein or a fragment thereof of the invention, as well as other molecules identified by the screening assays disclosed herein, can be administered for the treatment of a flavivirus-related disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhome, Pa., 1994; and Peptide And Protein Drug Delivery (Advances In Parenteral Sciences, Vol. 4), 1991, M. Dekker, New York.

In the embodiments of the present invention, antibody fragments are not preferred, specifically antibody fragments lacking an Fc region. Peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of a flavivirus (or a protein or a protein fragment thereof) in a sample. Preferably, the antibody contains a detectable label. Antibodies can be polyclonal, or more preferably, monoclonal. An intact antibody is preferred. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the fusion of an flavivirus to the cell membrane. Also provided are methods of identifying compounds useful to treat flavivirus infection. The invention also encompasses compounds identified using the screening assays described herein.

For example, the invention provides assays for screening candidate or test compounds which modulate the interaction between the flavivirus and the cell membrane. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409.).

In one embodiment, a candidate compound is introduced to an antibody-antigen complex and determining whether the candidate compound disrupts the antibody-antigen complex, wherein a disruption of this complex indicates that the candidate compound modulates the interaction between a flavivirus and the cell membrane. For example, the antibody may be monoclonal antibody mAb11, mAb11-LALA, or any variant thereof, and the antigen may be located on an envelope protein of a flavivirus (i.e., West Nile virus protein E).

In another embodiment, at least one flavivirus envelope protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat a flavivirus-related disease or disorder, e.g. Dengue fever. For example, the at least one flavivirus protein may be provided as a flavivirus molecule.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a flavivirus neutralizing antibody, such as monoclonal antibody Ab-11 or any variant thereof wherein the Fc region is modified such that it has reduced binding or does not bind to the Fc-gamma receptor. Additionally, the antigen may be a flavivirus envelope protein, or a portion thereof.

The screening methods disclosed herein may be performed as a cell-based assay or as a cell-free assay. The cell-free assays of the invention are amenable to use of both the soluble form or the membrane-bound form of the proteins and fragments thereof. In the case of cell-free assays comprising the membrane-bound forms of the proteins, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody or the antigen (e.g. the can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, an assay can be performed in which a flavivirus envelope protein (e.g., West Nile virus protein E) or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest bound to the immobilized polypeptide is subsequently incubated with a second, labeled antibody or antibody bound to a coupling agent such as biotin or avidin. This second antibody may be another anti-flavivirus antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

An exemplary method for detecting the presence or absence of a flavivirus (in a biological sample involves obtaining a biological sample from a test subject and contacting the biological sample with a labeled monoclonal antibody according to the invention such that the presence of the flavivirus is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect an flavivirus in a biological sample in vitro as well as in vivo. For example, in vitro techniques for detection of a flavivirus include enzyme linked immunosorbent assays (ELISAs), Western blots, immunoprecipitations, and immunofluorescence. Furthermore, in vivo techniques for detection of a flavivirus include introducing into a subject a labeled anti-flavivirus antibody. For example, the antibody can be labeled with a radioactive marker whose presence and location in a subject can be detected by standard imaging techniques.

In one embodiment, the biological sample contains protein molecules from the test subject. One preferred biological sample is a peripheral blood leukocyte sample isolated by conventional means from a subject.

The invention also encompasses kits for detecting the presence of a flavivirus in a biological sample. For example, the kit can comprise: a labeled compound or agent capable of detecting a flavivirus (e.g., an anti-flavivirus monoclonal antibody) in a biological sample; means for determining the amount of a flavivirus in the sample; and means for comparing the amount of a flavivirus in the sample with a standard. The compound or agent can be packaged in a suitable container. The kit can further comprise instructions for using the kit to detect a flavivirus in a sample.

Passive Immunization

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using neutralizing human monoclonal antibodies could provide an immediate treatment strategy for emergency prophylaxis and treatment of flavivirus infection and related diseases and disorders while the alternative and more time-consuming development of vaccines and new drugs in underway.

Subunit vaccines potentially offer significant advantages over conventional immunogens. They avoid the safety hazards inherent in production, distribution, and delivery of conventional killed or attenuated whole-pathogen vaccines. Furthermore, they can be rationally designed to include only confirmed protective epitopes, thereby avoiding suppressive T epitopes (see Steward et al., J. Virol. 69:7668 (1995)) or immunodominant B epitopes that subvert the immune system by inducing futile, non-protective responses (e.g. "decoy" epitopes). (See Garrity et al., J. Immunol. 159:279 (1997)).

Moreover, those skilled in the art will recognize that good correlation exists between the antibody neutralizing activity in vitro and the protection in vivo for many different viruses, challenge routes, and animal models. (See Burton, Natl. Rev. Immunol. 2:706-13 (2002); Parren et al., Adv. Immunol. 77:195-262 (2001)). The data presented herein demonstrate that the mAb-11 human monoclonal antibody and other mAb variants can be further developed and tested in in vivo animal studies to determine its clinical utility as a potent ADE inhibitor for prophylaxis and treatment of flavivirus infection and related diseases and disorders.

Antigen-Ig Chimeras in Vaccination

It has been over a decade since the first antibodies were used as scaffolds for the efficient presentation of antigenic determinants to the immune systems. (See Zanetti, Nature 355:476-77 (1992); Zaghouani et al., Proc. Natl. Acad. Sci. USA 92:631-35 (1995)). When a peptide is included as an integral part of an IgG molecule (e.g., the 11A or 256 IgG1 monoclonal antibody described herein), the antigenicity and immunogenicity of the peptide epitopes are greatly enhanced as compared to the free peptide. Such enhancement is possibly due to the antigen-IgG chimeras longer half-life, better presentation and constrained conformation, which mimic their native structures.

Moreover, an added advantage of using an antigen-Ig chimera is that either the variable or the Fc region of the antigen-Ig chimera can be used for targeting professional antigen-presenting cells (APCs). To date, recombinant Igs have been generated in which the complementarity-determining regions (CDRs) of the heavy chain variable gene ($V_H$) are replaced with various antigenic peptides recognized by B or T cells. Such antigen-Ig chimeras have been used to induce both humoral and cellular immune responses. (See Bona et al., Immunol. Today 19:126-33 (1998)).

Chimeras with specific epitopes engrafted into the CDR3 loop have been used to induce humoral responses to either HIV-1 gp120 V3-loop or the first extracellular domain (D1) of human CD4 receptor. (See Lanza et al., Proc. Natl. Acad. Sci. USA 90:11683-87 (1993); Zaghouani et al., Proc. Natl. Acad. Sci. USA 92:631-35 (1995)). The immune sera were able to prevent infection of CD4 SupT1 cells by HIV-1MN (anti-gp120 V3C) or inhibit syncytia formation (anti-CD4-D1). The CDR2 and CDR3 can be replaced with peptide epitopes simultaneously, and the length of peptide inserted can be up to 19 amino acids long.

Alternatively, one group has developed a "troybody" strategy in which peptide antigens are presented in the loops of the Ig constant (C) region and the variable region of the chimera can be used to target IgD on the surface of B-cells or MHC class II molecules on professional APCs including B-cells, dendritic cells (DC) and macrophages. (See Lunde et al., Biochem. Soc. Trans. 30:500-6 (2002)).

An antigen-Ig chimera can also be made by directly fusing the antigen with the Fc portion of an IgG molecule. You et al., Cancer Res. 61:3704-11 (2001) were able to obtain all arms of specific immune response, including very high levels of antibodies to hepatitis B virus core antigen using this method.

DNA Vaccination

DNA vaccines are stable, can provide the antigen an opportunity to be naturally processed, and can induce a longer-lasting response. Although a very attractive immunization strategy, DNA vaccines often have very limited potency to induce immune responses. Poor uptake of injected DNA by professional APCs, such as dendritic cells (DCs), may be the main cause of such limitation. Combined with the antigen-Ig chimera vaccines, a promising new DNA vaccine strategy based on the enhancement of APC antigen presentation has been reported (see Casares, et al., Viral Immunol. 10:129-36 (1997); Gerloni et al., Nat. Biotech. 15:876-81 (1997); Gerloni et al., DNA Cell Biol. 16:611-25 (1997); You et al., Cancer Res. 61:3704-11 (2001)), which takes advantage of the presence of Fc receptors (FcγRs) on the surface of DCs.

It is possible to generate a DNA vaccine encoding an antigen (Ag)-Ig chimera. Upon immunization, Ag-Ig fusion proteins will be expressed and secreted by the cells taking up the DNA molecules. The secreted Ag-Ig fusion proteins, while inducing B-cell responses, can be captured and internalized by interaction of the Fc fragment with FcγRs on DC surface, which will promote efficient antigen presentation and greatly enhance antigen-specific immune responses. Applying the same principle, DNA encoding antigen-Ig chimeras carrying a functional anti-MHC II specific scFv region gene can also target the immunogens to all three types of APCs. The immune responses could be further boosted with use of the same protein antigens generated in vitro (i.e., "prime and boost"), if necessary. Using this strategy, specific cellular and humoral immune responses against infection of flavivirus were accomplished through intramuscular (i.m.) injection of a DNA vaccine. (See Casares et al., Viral. Immunol. 10:129-36 (1997)).

Vaccine Compositions

Therapeutic or prophylactic compositions are provided herein, which generally comprise mixtures of one or more monoclonal antibodies or ScFvs and combinations thereof. The prophylactic vaccines can be used to prevent a flavivirus infection and the therapeutic vaccines can be used to treat individuals following a flavivirus infection. Prophylactic uses include the provision of increased antibody titer to a flavivirus in a vaccination subject. In this manner, subjects at high risk of contracting flavivirus (i.e., in subtropical regions where viral-carrying mosquitos thrive) can be provided with passive immunity to a flavivirus.

These vaccine compositions can be administered in conjunction with ancillary immunoregulatory agents. For example, cytokines, lymphokines, and chemokines, including, but not limited to, IL-2, modified IL-2 (Cys125→Ser125), GM-CSF, IL-12, γ-interferon, IP-10, MIP1β, and RANTES.

Methods of Immunization

The vaccines of the present invention have superior immunoprotective and immunotherapeutic properties over other anti-viral vaccines.

The invention provides a method of immunization, e.g., inducing an immune response, of a subject. A subject is immunized by administration to the subject a composition containing a membrane fusion protein of a pathogenic enveloped virus. The fusion protein is coated or embedded in a biologically compatible matrix.

The fusion protein is glycosylated, e.g. contains acarbohydrate moiety. The carbohydrate moiety may be in the form of a monosaccharide, disaccharide(s). oligosaccharide(s), polysaccharide(s), or their derivatives (e.g. sulfo- or phospho-substituted). The carbohydrate is linear or branched. The carbohydrate moiety is N-linked or O-linked to a polypeptide. N-linked glycosylation is to the amide nitrogen of asparagine side chains and O-linked glycosylation is to the hydroxy oxygen of serine and threonine side chains.

The carbohydrate moiety is endogenous to the subject being vaccinated. Alternatively, the carbohydrate moiety is exogenous to the subject being vaccinated. The carbohydrate moiety is a carbohydrate moieties that are not typically expressed on polypeptides of the subject being vaccinated. For example, the carbohydrate moieties are plant-specific carbohydrates. Plant specific carbohydrate moieties include for example N-linked glycan having a core bound α1,3 fucose or a core bound β1,2 xylose. Alternatively, the carbohydrate moiety are carbohydrate moieties that are expressed on polypeptides or lipids of the subject being vaccinate. For example many host cells have been genetically engineered to produce human proteins with human-like sugar attachments.

For example, the fusion protein is a trimeric hemagglutinin protein. Optionally, the hemagglutinin protein is produced in a non-mammalian cell such as a plant cell.

The subject is at risk of developing or suffering from a viral infection. Flavivirus family members include, for example West Nile virus, Dengue virus (serotypes 1-4), St. Louis encephalitis virus, yellow fever virus, Japanese encephalitis virus, or Murray Valley encephalitis virus. For example, the subject has traveled to regions or countries in which other flaviviral infections have been reported.

The methods described herein lead to a reduction in the severity or the alleviation of one or more symptoms of a viral infection. Infections are diagnosed and or monitored, typically by a physician using standard methodologies. A subject requiring immunization is identified by methods know in the art. For example subjects are immunized as outlined in the CDC's General Recommendation on Immunization (51(RR02) pp 1-36) Cancer is diagnosed for example by physical exam, biopsy, blood test, or x-ray.

The subject is e.g., any mammal, e.g., a human, a primate, mouse, rat, dog, cat, cow, horse, pig, a fish or a bird.

The treatment is administered prior to diagnosis of the infection. Alternatively, treatment is administered after diagnosis. Efficaciousness of treatment is determined in association with any known method for diagnosing or treating the particular disorder or infection. Alleviation of one or more symptoms of the disorder indicates that the compound confers a clinical benefit.

Methods of Treatment

The invention provides for both prophylactic and therapeutic methods of treating a subject at risk of (or susceptible to) a flavivirus-related disease or disorder. Such diseases or disorders include but are not limited to, e.g., fever, meningitis, encephalitis, yellow fever, dengue fever.

Prophylactic Methods

In one aspect, the invention provides methods for preventing a flavivirus-related disease or disorder in a subject by administering to the subject a monoclonal antibody of the invention or an agent identified according to the methods of the invention. For example, monoclonal antibody mAb-11, mAb11-LALA, and any variants thereof, wherein the Fc region is modified thereby reducing or abrogating binding to the Fc-gamma receptor, may be administered in therapeutically effective amounts. Optionally, two or more anti-flaviviruses antibodies are co-administered.

Subjects at risk for a flavivirus-related diseases or disorders include patients who have been exposed to the flavivirus from an infected arthropod (i.e., mosquito or tick). For example, the subjects have traveled to regions or countries of the world in which other flavivirus infections have been reported and confirmed. Administration of a prophylactic agent can occur prior to the manifestation of symptoms characteristic of the flaviviru-related disease or disorder, such that a disease or disorder is prevented or, alternatively, delayed in its progression.

The appropriate agent can be determined based on screening assays described herein. Alternatively, or in addition, the agent to be administered is a monoclonal antibody that neutralizes a flavivirus that has been identified according to the methods of the invention. In some embodiments, the antibody of the present invention can be administered with other antibodies or antibody fragments known to neutralize flaviviruses. Administration of said antibodies can be sequential, concurrent, or alternating.

Therapeutic Methods

Another aspect of the invention pertains to methods of treating a flavivirus-related disease or disorder in a patient. In one embodiment, the method involves administering an agent (e.g., an agent identified by a screening assay described herein and/or monoclonal antibody identified according to the methods of the invention), or combination of agents that neutralize the flavivirus to a patient suffering from the disease or disorder.

Combinatory Methods

The invention provides treating a flavivirus-related disease or disorder, such as West Nile fever, meningitis, Dengue fever, yellow fever or encephalitis, in a patient by administering two or more antibodies, such as mAb11-LALA or a variant of mAb11, wherein the Fc region of said variant does not bind or has reduced binding to the Fc gamma receptor, with other flavivirus neutralizing antibodies known in the art, such as mAb11. In another embodiment, the invention provides methods for treating a flavivirus-related disease or disorder in a patient by administering an antibody of the present invention, such as mAb11-LALA or a mAb11 variant as described herein, with any anti-viral agent known in the art. Anti-viral agents can be peptides, nucleic acids, small molecules, inhibitors, or RNAi.

The invention will be further described in the following examples, which do not limit the scope of the invention described in the claims.

EXAMPLES

Example 1: Prophylaxis Against Lethal Dengue-2 Virus Infection in Mice

Here is described a study examining the prophylactic effect of administration of the mAb11 antibody (both wild-type and the mutated form with modified Fc region) in mice. Forty mice were assessed in this study, and were divided into 5 groups containing 8 mice each. In Group 1, the mice were administered an isotype control IgG control antibody. Group 2 was administered 250 ug/mouse (~12.5 mg/kg) of wild-type mAb11. Group 3 was administered 50 ug/mouse (~2.5 mg/kg) of wild-type mAb11 (wt mAb). Group 4 was administered 250 ug/mouse (~12.5 mg/kg) of mAb11 with a LALA mutation in its Fc region (mut mAb). Group 5 was administered 50 ug/mouse (~2.5 mg/kg) of mAb11 with a LALA mutation in its Fc region (mut mAb).

After a period of time after administration of the antibody treatment (control, wildtype mAb11 or mutant mAb11), for example, 4 hours or 24 hours, the mice were injected with a lethal dose of Dengue-2 virus. The mice were then observed daily over 10 days for a variety of factors, such as weight loss, morbidity, and clinical scores that include appearance (coat and eye appearance), mobility, and attitude (and as illustrated in the table below).

TABLE 1

| Clinical Score | | | |
|---|---|---|---|
| Score | Initials | Description | Appearance, Mobility, and Attitude |
| 1 | H | Healthy | Smooth coat and bright eyes. Active, scurrying, and burrowing. Alert |
| 2 | SR | Slightly ruffled | Slightly ruffled coat (usually around head/neck). Active, scurrying, and burrowing. Alert |
| 3 | R | Ruffled | Ruffled coat throughout body - "wet" appearance. Active, scurrying, and burrowing. Alert |
| 4 | S | Sick | Very ruffled coat. Slightly closed, inset eyes. Walking, but no scurrying. Mildly lethargic |
| 5 | VS | Very sick | Very ruffled coat. Closed, inset eyes. Slow to no movement. Will return upright if put on its side. Extremely lethargic |
| 6 | E | Euthanize | Very ruffled coat. Closed, inset eyes. |
| 7 | D | Deceased | Moribund. Requires immediate euthanasia. No movement or uncontrolled spastic movements. Will not return upright if put on its side. Completely unaware or in noticeable distress |

Mice were euthanized if they scored at 5 or above and/or when they reached 20% weight loss.

Figure 3:
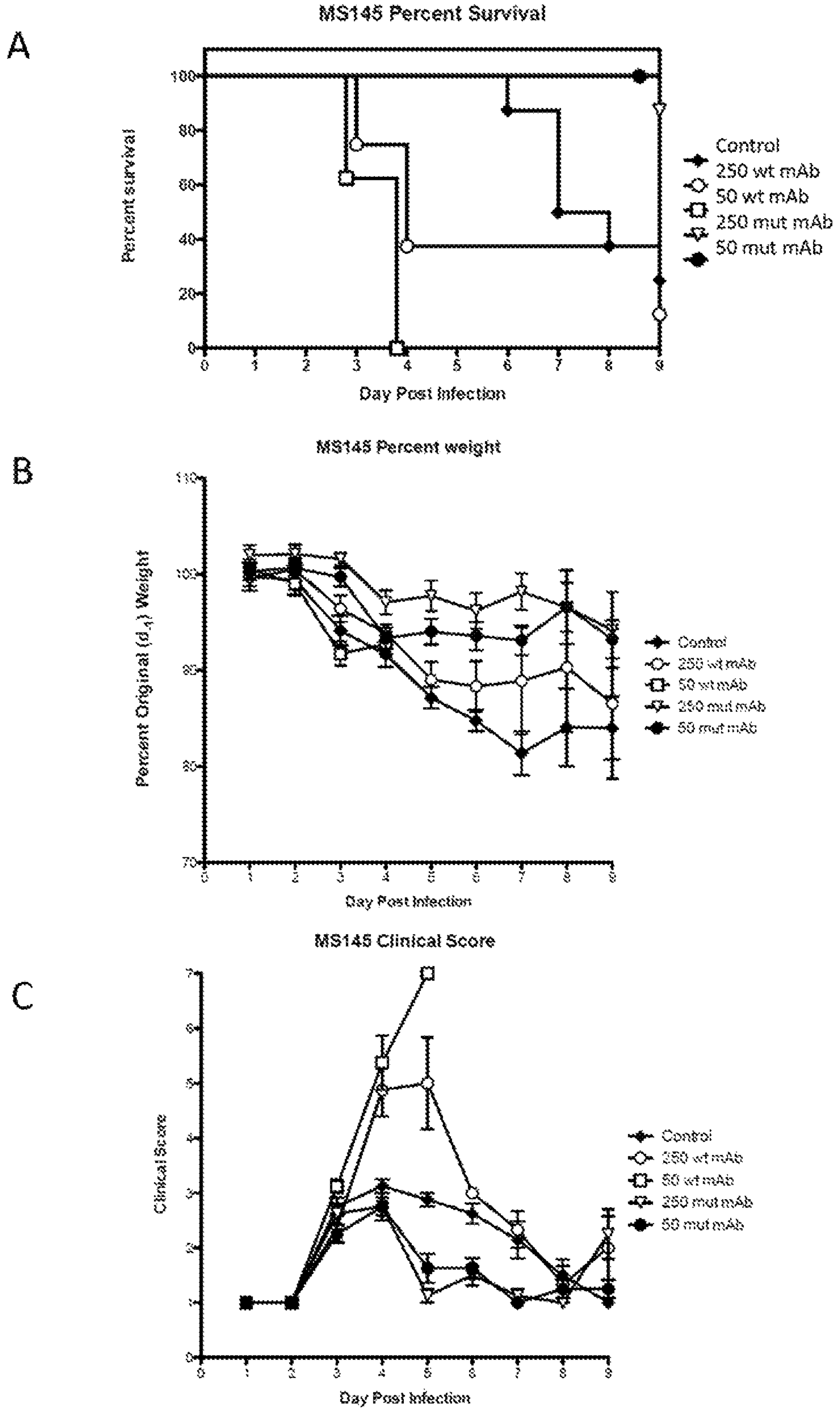
FIG. 3 is a series of three graphs showing the mAb11 (LALA) protection against lethal Dengue 2 virus infection. (A) Kaplan Meier survival curve compares the survival of mice administered with mAb11 with wild-type (wt) or mutant (mut) Fc regions. (B) Percent of original weight was monitored in mice administered with mAb11 with wild-type (wt) or mutant (mut) Fc regions. (C) Clinical scores were determined based on appearance, mobility and general attitude of the mice administered with mAb11 with wild-type (wt) or mutant (mut) Fc regions.

Study results were quantified and presented in FIG. 3. Specifically, FIG. 3A shows the Kaplan-Meier curves demonstrating the survival rate of the different groups of mice. The results show that control antibody and both dosages of wild-type mAb11 were not effective at protecting the mice from disease-related death/euthanization. In contrast, all of the mice receiving either dosage of the mutant mAb11 of the present invention survived the lethal dose infection. These results demonstrate the mutant mAb11 has prophylactic efficacy for flaviviral infection, especially compared to the wild-type antibody.

When comparing percent weight loss from before infection (FIG. 3B), animals administered mutant mAb11 lost less weight than animals administered control antibody or wild-type mAb11 lost weight over the course of the study. The clinical score analysis combine other qualitative observations regarding the appearance and attitude of the subjects to score the degree of observed health of the animals. As shown in FIG. 3C, the health of the animals receiving control or wild-type mAb11 quickly declined (clinical score numbers increased to above 4), while the animals that received the mutant mAb11 remained healthy, alert, and mobile even after 10 days of infection.

Taken together, all of these results indicate that the mutant mAb11 effectively prevented flaviviral infection-associated death, delayed progression of the symptoms of the disease, and had an overall prophylactic effect on mice infected with Dengue virus.

Example 2: Comparison Between Antibodies Derived from Mammalian Cells and Plant Cells As described herein, the antibodies of the present invention can be produced in transgenic plants. Other studies have shown that humanized antibodies suitable for administration for treatment in humans have been successfully produced in plants. Moreover, therapeutic antibody production in plants is an inexpensive and efficient alternative to antibody production in mammalian cells, and moreover, lacks animal pathogenic contaminants. To examine the efficacy of the mAb11 antibody of the present invention (containing the LALA mutation in the Fc region; mutAb) the antibodies produced from mammalian expression system and from plant (tobacco plant) were compared in vivo.

A129 mice were used for in this study. A129 mice lack IFN at/3 receptors, which are required for restricting viral replication in the central nervous system. A129 mice represent the most stringent model in the field for recapitulating human disease with regard to flaviviral infection. A129 mice infected with 1 PFU (plaque forming units) of Dengue virus causes paralysis. (Prestwood et al., J. Virol, 2012, Forty-five mice were assessed in this study, and were divided into 5 groups containing 9 mice each. In Group 1, the mice were administered a control IgG antibody. The control antibody used was Z-MAB (Zero-binding monoclonal antibody; AB Biosciences). Group 2 was administered 250 ug/mouse (~12.5 mg/kg) of mAb11 with a LALA mutation in its Fc region (mut mAb) produced in a mammalian expression system (mutAb mammalian). Group 3 was administered 50 ug/mouse (~2.5 mg/kg) of mutant mAb11 produced in a mammalian expression system. Group 4 was administered 250 ug/mouse (~12.5 mg/kg) of mutant mAb produced in a plant expression system (mutAb plant). Group 5 was administered 50 ug/mouse (~2.5 mg/kg) of mutant mAb11 produced in a plant expression system.

Mice were administered in the dosages of antibody as described above, then challenged with a lethal dose of Dengue virus. The mice were then observed daily over 20 days for a variety of factors, such as weight loss, morbidity, and clinical scores that include appearance (coat and eye appearance), mobility, and attitude (as described in Table 1).

Figure 4:
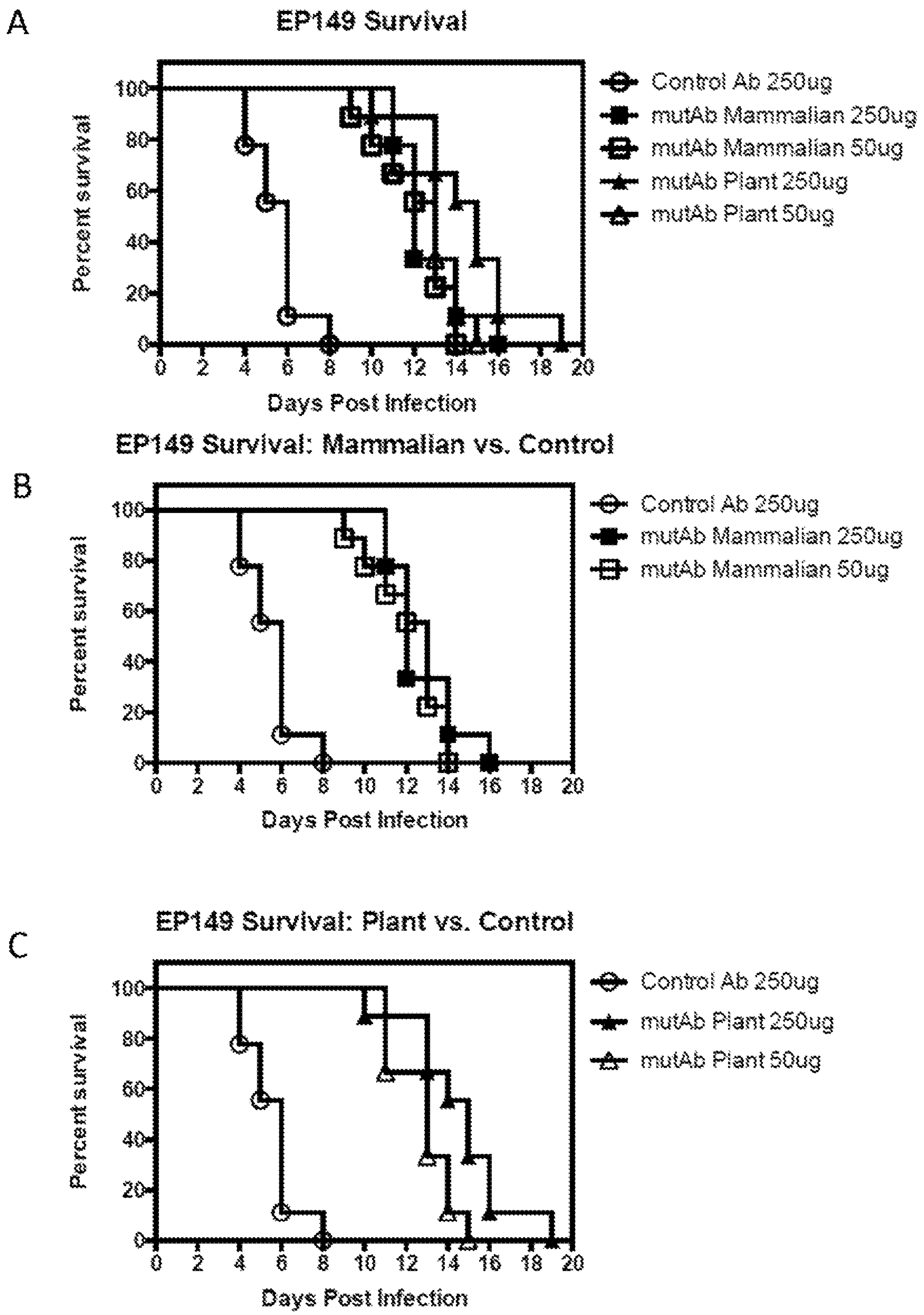
FIG. 4 is a series of three graphs comparing the survival rate of mice administered mammalian mAb11 with LALA mutation (mutAb) derived from mammalian cells or plant cells, and then challenged with lethal Dengue 2 virus infection. (A) Mammalian-derived mutant mAb11 antibody compared to plant-derived mutant mAb11 antibody. (B) Mammalian-derived mutant mAb11 antibody compared to control antibody. (C) Plant-derived mutant mAb11 antibody compared to control antibody.
Figure 5:
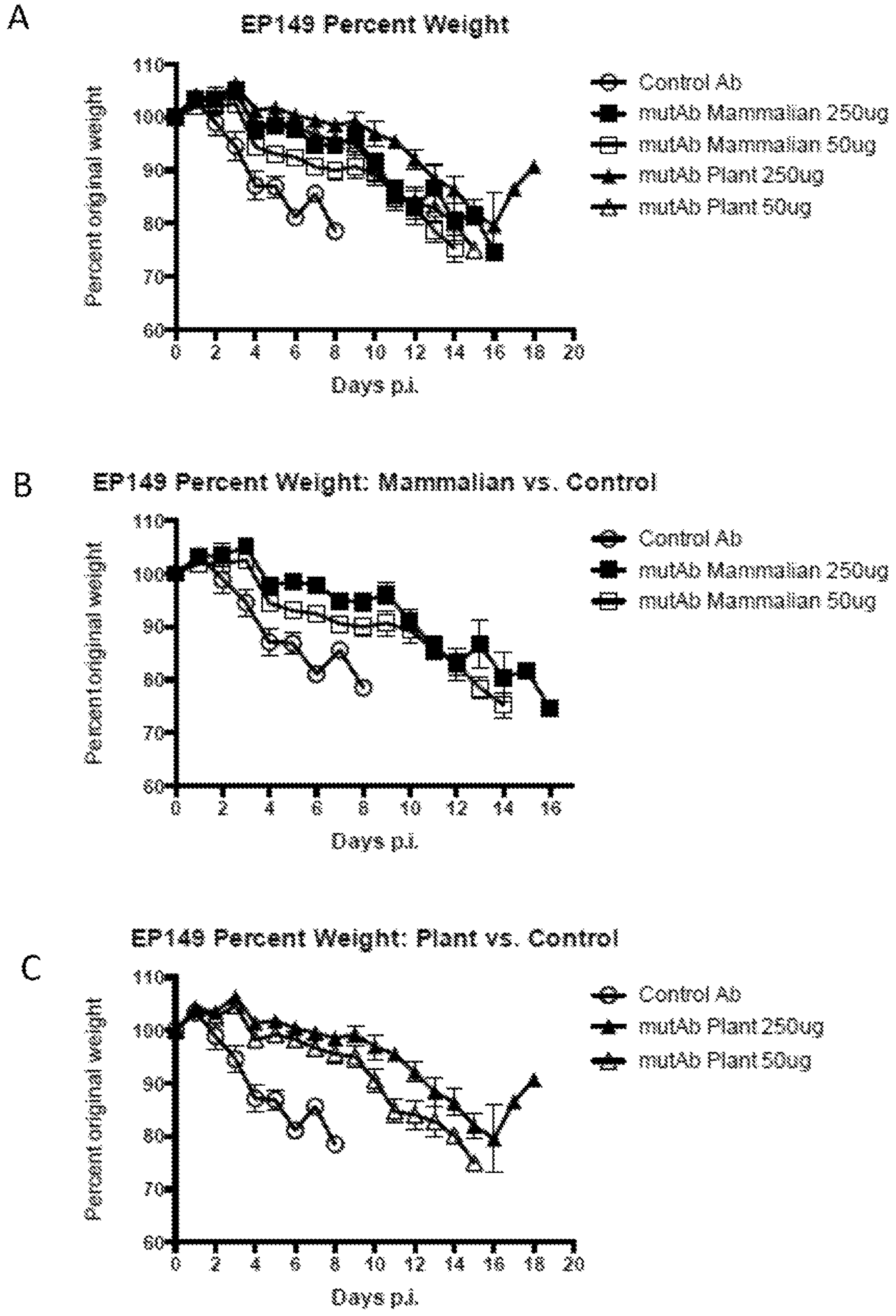
FIG. 5 is a series of three graphs comparing the percent weight of mice administered mammalian mAb11 with LALA mutation (mutAb) derived from mammalian cells or plant cells, and then challenged with lethal Dengue 2 virus infection. (A) Mammalian-derived mutant mAb11 antibody compared to plant-derived mutant mAb11 antibody. (B) Mammalian-derived mutant mAb11 antibody compared to control antibody. (C) Plant-derived mutant mAb11 antibody compared to control antibody.
Figure 6:
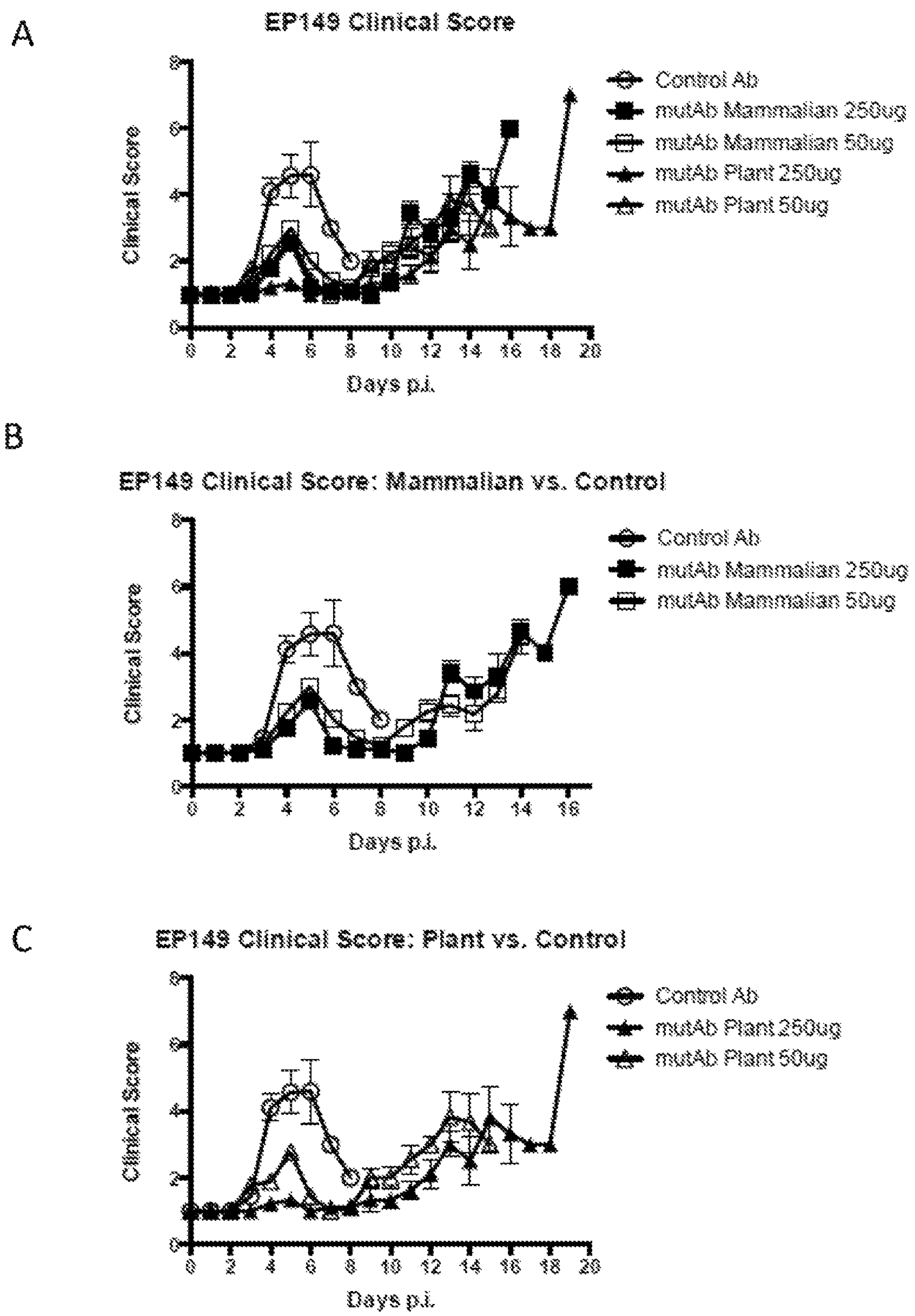
FIG. 6 is a series of three graphs comparing the clinical score of mice administered mammalian mAb11 with LALA mutation (mutAb) derived from mammalian cells or plant cells, and then challenged with lethal Dengue 2 virus infection. (A) Mammalian-derived mutant mAb11 antibody compared to plant-derived mutant mAb11 antibody. (B) Mammalian-derived mutant mAb11 antibody compared to control antibody. (C) Plant-derived mutant mAb11 antibody compared to control antibody.

The results of these studies are summarized in FIGS. 4, 5 and 6. FIG. 5 shows the overall survival of mice. Both doses of mutant mAb11 produced from mammalian systems demonstrated protective effect against viral infection, compared to control (FIG. 4A). Similar to the results shown in Example 1 and FIG. 3, all mice administered the mutAb antibody survived beyond day 10 of the study. Both doses of mutAb from plant also demonstrated protective effect, as shown in Figure B. Comparison between the two mutAb from mammalian and plant is shown in FIG. 3, which shows that the mutAb from plants were just as effective, if not more so, in protecting the mice from disease progression and death.

FIG. 5 shows the percent weight loss in animals over the course of the study. Both mutAb mammalian and mutAb plant antibodies both protected mice from weight loss in comparison to the control antibody (FIGS. 5B and 5C). Comparison between mammalian and plant-derived mutAb showed no significant difference between weight loss as a result of the antibody production method (FIG. 5A).

FIG. 6 shows the clinical scores of the animals over the course of the study. Administration of mutAb mammalian and mutAb plant antibodies protected mice from progression or severity of symptoms compared to control antibody (FIGS. 6B and 6C). Comparison between mammalian and plant-derived mutAb showed that the two antibodies performed similarly, with the mice receiving the higher dosage of plant-derived mutAb (250 ug) showing slightly better overall health as measured by the clinical scores (FIG. 6A).

Taken together, these results show that production of the mutant antibodies of the present invention were just as effective at protection and reducing severity of the disease as the antibodies produced by standard mammalian expression systems. For some of the measured parameters, particularly at high doses of the mutAb plant-derived antibody, the plant-derived antibodies showed to have a slightly increased therapeutic effect in comparison to the mammalian-derived antibodies. Thus, plant-derived antibodies of the present invention would be useful for the protection and treatment of flaviviral infection.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated humanized monoclonal antibody comprising:

a $V_H$ amino acid sequence having SEQ ID NO: 1, a $V_L$ amino acid sequence having SEQ ID NO: 3, and a modified Fc region having mutations at amino acid positions 234 and 235, such that the Fc region does not bind to the Fcγ receptor, wherein the mutations are L234A and L235A wherein positions 234 and 235 corresponds to positions 240 and 241 of SEQ ID NO: 20; and wherein the antibody binds and neutralizes a flavivirus.

2. An isolated humanized monoclonal antibody comprising:

a $V_H$ encoded by the nucleotide sequence SEQ ID NO: 2, a $V_L$ encoded by the nucleotide sequence SEQ ID NO: 4, and a modified Fc region having mutations at amino acid positions 234 and 235, such that the Fc region does not bind to the Fcγ receptor, wherein the mutations are L234A and L235A wherein positions 234 and 235 corresponds to positions 240 and 241 of SEQ ID NO: 20; and wherein the antibody binds and neutralizes a flavivirus.

3. The antibody of claim 1 or claim 2, wherein said antibody does not contribute to an antibody-dependent enhancement of a flavivirus infection.

4. The antibody of claim 1 or 2, wherein the Fc region comprises the amino acid sequence of SEQ ID NO: 7 or SEQ ID NO: 13.

5. The antibody of claim 1 or claim 2, wherein the modified Fc region binds to the neonatal Fc receptor.

6. The antibody of claim 1 or claim 2, wherein the flavivirus is West Nile virus, Dengue virus (serotypes 1-4), St. Louis encephalitis virus, yellow fever virus, Japanese encephalitis virus, and Murray Valley encephalitis virus.

7. The antibody of claim 1 or claim 2, wherein said humanized monoclonal antibody is produced in a plant.

8. The antibody of claim 1 or claim 2 linked to a therapeutic agent.

9. The antibody of claim 8, wherein said therapeutic agent is a toxin, a radiolabel, a siRNA, a small molecule, or a cytokine.

10. The antibody of claim 9, wherein said cytokine is TGF-beta.

11. An isolated cell producing the antibody of claim 1 or claim 2.

12. A method of reducing antibody-dependent enhancement of a flavivirus infection comprising administering the antibody of claim 1 or claim 2 to a subject.

13. The method of claim 12, wherein said antibody is administered after a first infection by a flavivirus.

14. A method of treating or alleviating a symptom of a flavivirus infection, comprising administering to a subject in need thereof a composition comprising an antibody according to claim 1.

15. A method of delaying the onset of one or more symptoms of a flavivirus infection, comprising administering to a subject in need thereof a composition comprising an antibody according to claim 1.

16. The method of any claim 14, wherein said one or more symptom comprises weight loss, paralysis, fever, headache, nausea, vomiting, skin rash, and body aches.

17. The method of claim 12, wherein said flavivirus is West Nile virus, Dengue virus (serotypes 1-4), St. Louis encephalitis virus, yellow fever virus, Japanese encephalitis virus, or Murray Valley encephalitis virus.

18. A nucleic acid sequence comprising a nucleic acid sequence of SEQ ID NO: 2, 4 and 8.

19. A nucleic acid sequence encoding a polypeptide comprising SEQ ID NO: 1, 3 and 7.

20. A polypeptide comprising the amino acid sequence comprising SEQ ID NO: 1, 3 and 7.

21. A vector comprising the nucleic acid of claim 18 or 19.

22. An isolated cell comprising the vector of claim 21.

23. The isolated cell of claim 11, wherein said isolated cell is a plant cell.

24. The method of claim 15, wherein said one or more symptom comprises weight loss, paralysis, fever, headache, nausea, vomiting, skin rash, or body aches.

25. The method of claim 14, wherein said flavivirus is West Nile virus, Dengue virus (serotypes 1-4), St. Louis encephalitis virus, yellow fever virus, Japanese encephalitis virus, or Murray Valley encephalitis virus.

26. The method of claim 15, wherein said flavivirus is West Nile virus, Dengue virus (serotypes 1-4), St. Louis encephalitis virus, yellow fever virus, Japanese encephalitis virus, or Murray Valley encephalitis virus.

27. A nucleic acid sequence encoding a polypeptide comprising SEQ ID NOS: 1, 3 and 13.

28. A polypeptide comprising the amino acid sequence comprising SEQ ID NOS: 1, 3, and 13.

29. A method of treating or alleviating a symptom of a flavivirus infection, comprising administering to a subject in need thereof a composition comprising an antibody according to claim 2.

30. A method of delaying the onset of one or more symptoms of a flavivirus infection, comprising administering to a subject in need thereof a composition comprising an antibody according to claim 2.

31. The isolated cell of claim 22, wherein said isolated cell is a plant cell.

32. The method of claim 16, 17, 29, or 30 further comprising administering an anti-viral agent.

33. The method of claim 32, wherein the anti-viral agent is an antibody, an antibody linked to a therapeutic agent, or a small molecule.

34. The method of claim 32, wherein said antibody and the anti-viral agent are administered sequentially or concurrently.

* * * * *

```
                         SEQUENCE LISTING


<160> NUMBER OF SEQ ID NOS: 26

<210> SEQ ID NO 1
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 1

Thr Arg Val Leu Ser Gln Val Gln Leu Val Gln Ser Gly Ala Glu Val
1               5                   10                  15

Lys Lys Pro Gly Ala Ser Val Lys Val Ser Cys Lys Ala Ser Gly Tyr
            20                  25                  30

Thr Phe Ser Gly Tyr Ser Thr His Trp Leu Arg Gln Val Pro Gly Gln
        35                  40                  45

Gly Leu Glu Trp Ile Gly Trp Asp Asn Pro Ser Ser Gly Asp Thr Thr
    50                  55                  60

Tyr Ala Glu Asn Phe Arg Gly Arg Val Thr Leu Thr Arg Asp Thr Ser
65                  70                  75                  80

Ile Thr Thr Asp Tyr Leu Glu Val Arg Gly Leu Arg Ser Asp Asp Thr
                85                  90                  95

Ala Val Tyr Tyr Cys Ala Arg Gly Gly Asp Asp Tyr Ser Phe Asp His
            100                 105                 110

Trp Gly Gln Gly Thr Leu Val Thr Val Ser Ser
        115                 120


<210> SEQ ID NO 2
<211> LENGTH: 354
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (190)..(192)
```

<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t

<400> SEQUENCE: 2
caggtgcagc tggtgcagtc tggggctgag gtgaagaagc ctggggcctc agtgaaagtc 60
tnctgcaagg cttctggata caccttcagn ggctactcta cacactggct gcgacaggtn 120
cctggacagg gacttgagtg gattggatgg gacaacccta gtagtggtga cacgacctat 180
gnagagaatn nncggggcag ggtcaccntg accagggaca cgtccatcac cacagattac 240
ttggaagtga ggggtntaag atctgacgac acggccgtnt attattgngc cagaggngga 300
gatgactaca gctttgacca ttggggtcag ggcaccctgg tcaccgtctc ctca 354

<210> SEQ ID NO 3
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 3

Ser Ser Glu Leu Thr Gln Asp Pro Ala Val Ser Val Ala Leu Gly Gln
1 5 10 15

Thr Val Arg Ile Thr Cys Arg Gly Asp Ser Leu Arg Ser Tyr Tyr Ala
20 25 30

Ser Trp Tyr Gln Gln Lys Pro Gly Gln Ala Pro Val Leu Val Ile Tyr
35 40 45

Gly Glu Asn Asn Arg Pro Ser Gly Ile Pro Asp Arg Phe Ser Gly Ser
50 55 60

Ser Ser Gly Asp Thr Ala Ser Leu Thr Ile Thr Gly Ala Gln Ala Glu
65 70 75 80

Asp Glu Ala Asp Tyr Tyr Cys Asn Ser Arg Asp Ser Ser Asp His Leu
85 90 95

Leu Leu Phe Gly Gln Gly Thr Lys Leu
100 105

<210> SEQ ID NO 4
<211> LENGTH: 327
<212> TYPE: DNA
<213> ORGANISM: Artificial Sequence
<220> FEATURE:
<223> OTHER INFORMATION: Synthetic Oligonucleotide

<400> SEQUENCE: 4
tcttctgagc tgactcagga cccagctgtg tctgtggcct tgggacagac agtcaggatc 60

-continued

```
acatgccgag gagacagcct cagaagttat tatgcaagct ggtaccaaca gaagccagga    120

caggcccctg tacttgtcat ctatggtgaa aacaaccgac cctcagggat cccagaccga    180

ttctctggct ccagctcagg agacacagct tccttgacca tcactggggc tcaggcggaa    240

gatgaggctg actattactg taactcccgg gacagcagtg atcaccttct cctattcggt    300

ggagggacca agttgaccgt cctaggt                                        327


<210> SEQ ID NO 5
<211> LENGTH: 330
<212> TYPE: PRT
<213> ORGANISM: Homo sapiens

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

-continued 325 330

<210> SEQ ID NO 6
<211> LENGTH: 992
<212> TYPE: DNA
<213> ORGANISM: Homo sapiens

<400> SEQUENCE: 6
ctagcaccaa gggcccatcg gtcttccccc tggcaccctc ctccaagagc acctctgggg 60
gcacagcggc cctgggctgc ctggtcaagg actacttccc cgaaccggtg acggtgtcgt 120
ggaactcagg cgccctgacc agcggcgtgc acaccttccc ggctgtccta cagtcctcag 180
gactctactc cctcagcagc gtggtgaccg tgccctccag cagcttgggc acccagacct 240
acatctgcaa cgtgaatcac aagcccagca acaccaaggt ggacaagaaa gcagagccca 300
aatcttgtga caaaactcac acatgcccac cgtgcccagc acctgaactc ctggggggac 360
cgtcagtctt cctcttcccc ccaaaaccca aggacaccct catgatctcc cggacccctg 420
aggtcacatg cgtggtggtg gacgtgagcc acgaagaccc tgaggtcaag ttcaactggt 480
acgtggacgg cgtggaggtg cataatgcca agacaaagcc gcgggaggag cagtacaaca 540
gcacgtaccg tgtggtcagc gtcctcaccg tcctgcacca ggactggctg aatggcaagg 600
agtacaagtg caaggtctcc aacaaagccc tcccagcccc catcgagaaa accatctcca 660
aagccaaagg gcagccccga gaaccacagg tgtacaccct gcccccatcc cgggatgagc 720
tgaccaagaa ccaggtcagc ctgacctgcc tggtcaaagg cttctatccc agcgacatcg 780
ccgtggagtg ggagagcaat gggcagccgg agaacaacta caagaccacg cctcccgtgc 840
tggactccga cggctccttc ttcctctaca gcaagctcac cgtggacaag agcaggtggc 900
agcaggggaa cgtcttctca tgctccgtga tgcatgaggc tctgcacaac cactacacgc 960
agaagagcct ctccctgtct ccgggtaaat ga 992

<210> SEQ ID NO 7
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 7

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Ala Glu Pro Lys Ser Cys Asp Lys Thr His Thr Cys Pro Pro Cys
100 105 110

Pro Ala Pro Glu Ala Ala Gly Gly Pro Ser Val Phe Leu Phe Pro Pro
115 120 125

Lys Pro Lys Asp Thr Leu Met Ile Ser Arg Thr Pro Glu Val Thr Cys 130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 8
<211> LENGTH: 992
<212> TYPE: DNA
<213> ORGANISM: Artificial Sequence
<220> FEATURE:
<223> OTHER INFORMATION: Synthetic Oligonucleotide

<400> SEQUENCE: 8
ctagcaccaa gggcccatcg gtcttccccc tggcaccctc ctccaagagc acctctgggg 60
gcacagcggc cctgggctgc ctggtcaagg actacttccc cgaaccggtg acggtgtcgt 120
ggaactcagg cgccctgacc agcggcgtgc acaccttccc ggctgtccta cagtcctcag 180
gactctactc cctcagcagc gtggtgaccg tgccctccag cagcttgggc acccagacct 240
acatctgcaa cgtgaatcac aagcccagca acaccaaggt ggacaagaaa gcagagccca 300
aatcttgtga caaaactcac acatgcccac cgtgcccagc acctgaagcc gccgggggac 360
cgtcagtctt cctcttcccc ccaaaaccca aggacaccct catgatctcc cggacccctg 420
aggtcacatg cgtggtggtg gacgtgagcc acgaagaccc tgaggtcaag ttcaactggt 480
acgtggacgg cgtggaggtg cataatgcca agacaaagcc gcgggaggag cagtacaaca 540
gcacgtaccg tgtggtcagc gtcctcaccg tcctgcacca ggactggctg aatggcaagg 600
agtacaagtg caaggtctcc aacaaagccc tcccagcccc catcgagaaa accatctcca 660
aagccaaagg gcagccccga gaaccacagg tgtacaccct gcccccatcc cgggatgagc 720
tgaccaagaa ccaggtcagc ctgacctgcc tggtcaaagg cttctatccc agcgacatcg 780
ccgtggagtg ggagagcaat gggcagccgg agaacaacta caagaccacg cctcccgtgc 840
tggactccga cggctccttc ttcctctaca gcaagctcac cgtggacaag agcaggtggc 900
agcaggggaa cgtcttctca tgctccgtga tgcatgaggc tctgcacaac cactacacgc 960
agaagagcct ctccctgtct ccgggtaaat ga 992

<210> SEQ ID NO 9
<211> LENGTH: 97
<212> TYPE: PRT
<213> ORGANISM: Homo sapiens

<400> SEQUENCE: 9

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys

<210> SEQ ID NO 10
<211> LENGTH: 290
<212> TYPE: DNA
<213> ORGANISM: Homo sapiens

<400> SEQUENCE: 10
ctagcaccaa gggcccatcg gtcttccccc tggcaccctc ctccaagagc acctctgggg 60
gcacagcggc cctgggctgc ctggtcaagg actacttccc cgaaccggtg acggtgtcgt 120
ggaactcagg cgccctgacc agcggcgtgc acaccttccc ggctgtccta cagtcctcag 180
gactctactc cctcagcagc gtggtgaccg tgccctccag cagcttgggc acccagacct 240
acatctgcaa cgtgaatcac aagcccagca acaccaaggt ggacaagaaa 290

<210> SEQ ID NO 11
<211> LENGTH: 110
<212> TYPE: PRT
<213> ORGANISM: Homo sapiens

<400> SEQUENCE: 11

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys
100 105 110

-continued

<210> SEQ ID NO 12
<211> LENGTH: 330
<212> TYPE: DNA
<213> ORGANISM: Homo sapiens

<400> SEQUENCE: 12
gcacctgaac tcctgggggg accgtcagtc ttcctcttcc ccccaaaacc caaggacacc 60
ctcatgatct cccggacccc tgaggtcaca tgcgtggtgg tggacgtgag ccacgaagac 120
cctgaggtca agttcaactg gtacgtggac ggcgtggagg tgcataatgc caagacaaag 180
ccgcgggagg agcagtacaa cagcacgtac cgtgtggtca gcgtcctcac cgtcctgcac 240
caggactggc tgaatggcaa ggagtacaag tgcaaggtct ccaacaaagc cctcccagcc 300
cccatcgaga aaaccatctc caaagccaaa 330

<210> SEQ ID NO 13
<211> LENGTH: 110
<212> TYPE: PRT
<213> ORGANISM: Artificial Sequence
<220> FEATURE:
<223> OTHER INFORMATION: Synthetic Polypeptide

<400> SEQUENCE: 13

Ala Pro Glu Ala Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys
100 105 110

<210> SEQ ID NO 14
<211> LENGTH: 330
<212> TYPE: DNA
<213> ORGANISM: Artificial Sequence
<220> FEATURE:
<223> OTHER INFORMATION: Synthetic Oligonucleotide

<400> SEQUENCE: 14
gcacctgaag ccgccggggg accgtcagtc ttcctcttcc ccccaaaacc caaggacacc 60
ctcatgatct cccggacccc tgaggtcaca tgcgtggtgg tggacgtgag ccacgaagac 120
cctgaggtca agttcaactg gtacgtggac ggcgtggagg tgcataatgc caagacaaag 180
ccgcgggagg agcagtacaa cagcacgtac cgtgtggtca gcgtcctcac cgtcctgcac 240
caggactggc tgaatggcaa ggagtacaag tgcaaggtct ccaacaaagc cctcccagcc 300
cccatcgaga aaaccatctc caaagccaaa 330

<210> SEQ ID NO 15
<211> LENGTH: 107
<212> TYPE: PRT
<213> ORGANISM: Homo sapiens

<400> SEQUENCE: 15

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 16
<211> LENGTH: 324
<212> TYPE: DNA
<213> ORGANISM: Homo sapiens

<400> SEQUENCE: 16
gggcagcccc gagaaccaca ggtgtacacc ctgcccccat cccgggatga gctgaccaag 60
aaccaggtca gcctgacctg cctggtcaaa ggcttctatc ccagcgacat cgccgtggag 120
tgggagagca atgggcagcc ggagaacaac tacaagacca cgcctcccgt gctggactcc 180
gacggctcct tcttcctcta cagcaagctc accgtggaca agagcaggtg gcagcagggg 240
aacgtcttct catgctccgt gatgcatgag gctctgcaca accactacac gcagaagagc 300
ctctccctgt ctccgggtaa atga 324

<210> SEQ ID NO 17
<211> LENGTH: 16
<212> TYPE: PRT
<213> ORGANISM: Homo sapiens

<400> SEQUENCE: 17

Ala Glu Pro Lys Ser Cys Asp Lys Thr His Thr Cys Pro Pro Cys Pro
1               5                   10                  15

<210> SEQ ID NO 18
<211> LENGTH: 48
<212> TYPE: DNA
<213> ORGANISM: Homo sapiens

<400> SEQUENCE: 18
gcagagccca aatcttgtga caaaactcac acatgcccac cgtgccca 48

<210> SEQ ID NO 19
<211> LENGTH: 453
<212> TYPE: PRT
<213> ORGANISM: Homo sapiens

<400> SEQUENCE: 19

Thr Arg Val Leu Ser Gln Val Gln Leu Val Gln Ser Gly Ala Glu Val
1               5                   10                  15

Lys Lys Pro Gly Ala Ser Val Lys Val Ser Cys Lys Ala Ser Gly Tyr
            20                  25                  30

Thr Phe Ser Gly Tyr Ser Thr His Trp Leu Arg Gln Val Pro Gly Gln
        35                  40                  45

-continued

```
Gly Leu Glu Trp Ile Gly Trp Asp Asn Pro Ser Ser Gly Asp Thr Thr
    50                  55                  60

Tyr Ala Glu Asn Phe Arg Gly Arg Val Thr Leu Thr Arg Asp Thr Ser
65                  70                  75                  80

Ile Thr Thr Asp Tyr Leu Glu Val Arg Gly Leu Arg Ser Asp Asp Thr
                85                  90                  95

Ala Val Tyr Tyr Cys Ala Arg Gly Gly Asp Asp Tyr Ser Phe Asp His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Ala Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 20
<211> LENGTH: 453
<212> TYPE: PRT
<213> ORGANISM: Artificial Sequence
<220> FEATURE:
<223> OTHER INFORMATION: Synthetic Polypeptide

<400> SEQUENCE: 20

```
Thr Arg Val Leu Ser Gln Val Gln Leu Val Gln Ser Gly Ala Glu Val
1               5                   10                  15

Lys Lys Pro Gly Ala Ser Val Lys Val Ser Cys Lys Ala Ser Gly Tyr
            20                  25                  30

Thr Phe Ser Gly Tyr Ser Thr His Trp Leu Arg Gln Val Pro Gly Gln
        35                  40                  45

Gly Leu Glu Trp Ile Gly Trp Asp Asn Pro Ser Ser Gly Asp Thr Thr
    50                  55                  60

Tyr Ala Glu Asn Phe Arg Gly Arg Val Thr Leu Thr Arg Asp Thr Ser
65                  70                  75                  80

Ile Thr Thr Asp Tyr Leu Glu Val Arg Gly Leu Arg Ser Asp Asp Thr
                85                  90                  95

Ala Val Tyr Tyr Cys Ala Arg Gly Gly Asp Asp Tyr Ser Phe Asp His
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Ala Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365
```

```
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 21
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 21

Gly Tyr Ser Thr His
1               5


<210> SEQ ID NO 22
<211> LENGTH: 17
<212> TYPE: PRT
<213> ORGANISM: Artificial Sequence
<220> FEATURE:
<223> OTHER INFORMATION: Artificial Polypeptide

<400> SEQUENCE: 22

Trp Asp Asn Pro Ser Ser Gly Asp Thr Thr Tyr Ala Glu Asn Phe Arg
1               5                   10                  15

Gly


<210> SEQ ID NO 23
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 23

Gly Gly Asp Asp Tyr Ser Phe Asp His
1               5


<210> SEQ ID NO 24
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 24

Arg Gly Asp Ser Leu Arg Ser Tyr Tyr Ala Ser
1               5                   10


<210> SEQ ID NO 25
<211> LENGTH: 7
<212> TYPE: PRT
<213> ORGANISM: Artificial Sequence
<220> FEATURE:
<223> OTHER INFORMATION: Synthetic Polypeptide
```

-continued

```
<400> SEQUENCE: 25

Gly Glu Asn Asn Arg Pro Ser
1               5


<210> SEQ ID NO 26
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 26

Asn Ser Arg Asp Ser Ser Asp His Leu Leu Leu
1               5                   10
```